US007097998B2

(12) United States Patent
Koo et al.

(10) Patent No.: US 7,097,998 B2
(45) Date of Patent: Aug. 29, 2006

(54) Aβ$_{42}$ LOWERING AGENTS

(75) Inventors: Edward Hao Mang Koo, La Jolla, CA (US); Todd E. Golde, Ponte Vedra Beach, FL (US); Sascha Weggen, Mainz (DE)

(73) Assignees: The Regents of the University of California, Oakland, CA (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/928,925

(22) Filed: Aug. 27, 2004

(65) Prior Publication Data

US 2005/0089945 A1   Apr. 28, 2005

Related U.S. Application Data

(60) Division of application No. 10/012,606, filed on Dec. 7, 2001, now Pat. No. 6,911,466, which is a continuation-in-part of application No. PCT/US2001/11956, filed on Apr. 12, 2001.

(60) Provisional application No. 60/196,617, filed on Apr. 13, 2000.

(51) Int. Cl.
*A61K 38/00*   (2006.01)
*C12Q 1/37*    (2006.01)

(52) U.S. Cl. .............................. 435/23; 514/2
(58) Field of Classification Search ............... 435/7.2, 435/23; 514/305, 567, 569, 570, 2; 546/13, 546/137
See application file for complete search history.

(56) References Cited

U.S. PATENT DOCUMENTS

| 5,192,753 | A | 3/1993 | McGeer et al. |
| 5,434,170 | A | 7/1995 | Andrulis |
| 5,455,169 | A | 10/1995 | Mullan |
| 5,603,959 | A | 2/1997 | Horrobin et al. |
| 5,643,960 | A | 7/1997 | Breitner et al. |
| 5,695,774 | A | 12/1997 | Clark |
| 6,025,395 | A | 2/2000 | Breitner et al. |
| 6,160,018 | A | 12/2000 | Wechter et al. |
| 6,160,618 | A | 12/2000 | Garner |
| 6,184,248 | B1 | 2/2001 | Lee et al. |
| 6,255,347 | B1 | 7/2001 | Xiaotao et al. |
| 6,469,055 | B1 | 10/2002 | Lee et al. |

FOREIGN PATENT DOCUMENTS

WO     WO 01/78721    10/2001

OTHER PUBLICATIONS

Breitner et al. 1994. Neurology, vol. 44, pp. 227-232.*
Netland et al. 1998. Neurobiology of Aging, vol. 19, pp. 201-204.*
Rogers et al 1993. Neurology, vol. 43, pp. 1609-1611.*

Akoho et al., "A Study on Binding Modes of Nonsteroidal Anti-inflammatory Drugs to COX1 and COX2 as Obtained by Dock4.0," *J. Chem. Software*, 1999, 5(3):1-13.
Amin et al., "The pleiotropic functions of aspirin: mechanisms of action," *Cell. Mol. Life Sci.*, 1999, 56:305-312.
Andreasen et al., "Cerebrospinal Fluid β-Amyloid$_{(1-42)}$ in Alzheimer Disease," *Arch. Neurol.*, 1999, 56:673-680.
Bayly et al., "Structure-Based Design of Cox-2 Selectivity Into Flurbiprofen," *Bioor. Med. Chem. Lett.*, 1999, 9:307-312.
Bickford et al., "Long-Term Treatment of Male F344 Rats with Deprenyl: Assessment of Effects on Longevity, Behavior, and Brain Function," *Neurobiology of Aging*, 1997, 18(3):309-318.
Blacker et al., "The Genetics of Alzheimer Disease," *Arch. Neurol.*, 1998, 55:194-296.
Braak et al., "Neuropathological stageing of Alzheimer-related changes," *Acta. Neuropathol.*, 1991, 82:239-259.
Breitner et al., "Delayed onset of Alzheimer's disease with nonsteroidal anti-inflammatory and histamine H2 blocking drugs," *Neurobiol. Aging*, 1995, 16(4):523-30.
Cammisuli et al., "Effects of extended electrical kindling on exploratory behavior and spatial learning," *Behav. Brain Res.*, 1997, 89:179-190.
Canaparo et al., "Determination Ibuprofen in human plasma by high-performance liquid chromatography: validation and application in pharmacokinetic study," *Biomed. Chromatogr.*, 2000, 14:219-226.
Chen et al., "A learning deficit related to age and β-amyloid plaques in a mouse model of Alzheimder's disease," *Nature*, 2000, 408:975-979.

(Continued)

*Primary Examiner*—Jon Weber
*Assistant Examiner*—Kailash C. Srivastava
(74) *Attorney, Agent, or Firm*—Jonathan A. Baker; Jay Z. Zhang; Myriad genetics IP Department

(57) ABSTRACT

The invention provides a method of preventing, delaying, or reversing the progression of Alzheimer's disease by administering an Aβ$_{42}$ lowering agent to a mammal under conditions in which levels of Aβ$_{42}$ are selectively reduced, levels of Aβ$_{38}$ are increased, and levels of Aβ$_{40}$ are unchanged. The invention provides methods and materials for developing and identifying Aβ$_{42}$ lowering agents. In addition, the invention provides methods for identifying agents that increase the risk of developing, or hasten progression of, Alzheimer's disease. The invention also provides compositions of Aβ$_{42}$ lowering agents and antioxidants, Aβ$_{42}$ lowering agents and non-selective secretase inhibitors, as well as Aβ$_{42}$ lowering agents and acetylcholinesterase inhibitors. The invention also provides kits containing Aβ$_{42}$ lowering agents, antioxidants, non-selective secretase inhibitors, and/or acetylcholinesterase inhibitors as well as instructions related to dose regimens for Aβ$_{42}$ lowering agents, antioxidants, non-selective secretase inhibitors, and acetylcholinesterase inhibitors.

22 Claims, 12 Drawing Sheets

OTHER PUBLICATIONS

Citron et al., "Evidence that the 42- and 40-amino acid forms of amyloid β protein are generated from the β-amyloid precursor protein by different protease activities," *Proc. Natl. Acad. Sci. USA*, 1996, 93:13170-13175.

Combs et al., "Inflammatory Mechanisms in Alzheimer's Disease: Inhibition of β-Amyloid-Stimulated Proinflammatory Responses and Neurotoxicity by PPARγ Agonists," *J. Neurosci.*, 2000, 20(2):558-567.

Corton et al., "Central Role of Peroxisome Proliferator-Activated Receptors in the Actions of Peroxisome Proliferators," *Annu. Rev. Pharmacol.*, 2000, 40:491-518.

Cotran et al., *Pathologic Basis of Disease*, Sixth Edition, 1999, W.B. Saunders Company, Philadelphia, p. 1332, Table. 30-2.

Cronstein et al., "Targets for Antiinflammatory Drugs," *Annu. Rev. Pharmacol. Toxicol.*, 1995, 35:449-462.

Cryer et al., "Cyclooxygenase-1 and Cyclooxygenase-2 Selectivity of Widely Used Nonsteroidal Anti-Inflammatory Drugs," *Am. J. Med.*, 1998, 104:413-421.

DeWitt, "Cox-2-Selective Inhibitors: The New Super Aspirins," *Mol. Pharmacol.*, 1999, 55(4):625-631.

Dubois et al., "Cyclooxygenase in biology and disease," *FASEB J.*, 1998, 12:1063-1073.

Eriksen et al., "NSAIDs and enantiomers of flurbiprofen target γ-secretase and lower Aβ42 in vivo," *J. Clin. Invest.*, 2003, 112(3):440-449.

Folstein et al., "Mini-Mental State"—A Practical Method for Grading the Cognitive State of Patients for the Clinician, *J. Psychiat. Res.*, 1975, 12:189-198.

Frautschy et al., "Animal Model—Microglial Response to Amyloid Plaques in APPsw Transgenic Mice," *Am. J. Pathol.*, 1998, 152:307-317.

Galasko et al., "An Inventory to Assess Activities of Daily Living for Clinical Trials in Alzheimer's Disease," *Alzheimer Disease and Associated Disorders*, 1997, 11(Suppl. 2):S33-S39.

Galasko et al., "High Cerebrospinal Fluid Tau and Low Amyloid β42 Levels in the Clinical Diagnosis of Alzheimer Disease and Relation to Apolipoprotein E Genotype," *Arch. Neurol.*, 1998, 55:937-945.

Halliday et al., "Alzheimer's Disease and Inflammation: A Review of Cellular and Therapeutic Mechanisms," *Clin. Exp. Pharmacol. Physiol.*, 2000, 27:1-8.

Haugabook et al., "Reduction of Aβ accumulation in the Tg2576 animal model of Alzheimer's disease after oral administration of the phosphatidylinositol kinase inhibitor wortmannin," *FASEB J.*, 2000, 12 pgs.

He et al., "PPARδ Is an APC-Regulated Target of Nonsteroidal Anti-Inflammatory Drugs," *Cell*, 1999, 99:335-345.

Higaki et al., "Inhibition of β-Amyloid Formation Identifies Proteolytic Precursors and Subcellular Site of Catabolism," *Neuron*, 1995, 14:651-659.

Hsiao et al., "Correlative Memory Deficits, Aβ Elevation, and Amyloid Plaques in Transgenic Mice," *Science*, 1996, 274:99-102.

Kalgutkar et al., "Biochemically based design of cyclooxygenase-2 (COX-2) inhibitors: Facile conversion of nonsteroidal antiinflammatory drugs to potent and highly selective COX-2 inhibitors," *Proc. Natl. Acad. Sci. USA*, 2000, 97(2):925-930.

Kalgutkar et al., "Ester and Amide Derivatives of the Nonsteroidal Antiinflammatory Drug, Indomethacin, as Selective Cyclooxygenase-2 Inhibitors," *J. Med. Chem.*, 2000, 43:2860-2870.

Kato et al., "Cyclooxygenase-1 and cyclooxygenase-2 selectivity of non-steroidal anti-inflammatory drugs: investigation using human peripheral monocytes," *Journal of Pharmacy and Pharmacology*, 2001, 53:1679-1685.

Kawarabayashi et al., "Age-Dependent Changes in Brain, CSF, and Plasma Amyloid β Protein in the Tg2576 Transgenic Mouse Model of Alzhelmer's Disease," *J. Neurosci.*, 2001, 21(2):372-381.

Khachaturinan, "Diagnosis of Alzheimer's Disease," *Arch. Neurol.*, 1985, 42:1097-1105.

Kitamura et al., "Increased Expression Cyclooxygenases and Peroxisom Proliferator-Activated Receptor-γ in Alzheimer's Disease Brains," *Biochem. Biophys. Res. Comm.*, 1999, 254:582-586.

Klafki et al., "The Carboxyl Termini of β-Amyloid Peptides 1-40 and 1-42 Are Generated by Distinct γSecretase Activities," *J. Biol. Chem.*, 1996, 271(45):28655-28659.

Koo et al., "Evidence That Production and Release of Amyloid β-Protein Involves the Endocytic Pathway," *J. Biol. Chem.*, 1994, 269(26):17386-17389.

Koo et al., "Trafficking of cell-surface amyloid β-protein perecursor," *J. Cell Sci.*, 1996, 109:991-998.

Kopan et al., "Signal trasduction by activated mNotch: Importance of proteolytic processing and its regulation by the extracellular domain," *Proc. Natl. Acad. Sci. USA*, 1996, 93:1683-1688.

Koup et al., "A Single and Multiple Dose Pharmacokinetc and Metabolism Study of Meclofenamate Sodium," *Biopham. Drug Dispos.*, 1990, 11:1-15.

Lewis et al., "Neurofibrillary tangles, amyotrophy and progressive motor disturbance in mice expressing mutant (P301L) tau protein," *Nature Genetics*, 2000, 25:402-405.

Lim et al., "Ibuprofen Suppresses Plaque Pathology and Inflammation in a Mouse Model for Alzheimer's Disease," *J. Neurosci.*, 2000, 20(15):5709-5714.

Lu et al., "A second cytotoxic proteolytic peptide derived ffrom a amyloid β-protein precursor," *Nature Medicine*, 2000, 6(4):397-404.

McGeer et al., "Anti-inflammatory drugs and Alzheimer disease," *Lancet*, 1990, 335(8696):1037.

McGeer et al., "Arthritis and anti-inflammatory agents as possible protective factors for Alzheimer' disease: a review of 17 epidemiologic studies," *Neurology*, 1996, 47(2):425-32.

McKhann et al., "Clinical diagnosis of Alzheimer's disease: Report of the NINCDS-ADRDA Work Group under the auspices of Department of Health and Human Services Task Force on Alzheimer's Disease," *Neurology*, 1984, 34(7):939-944.

McLendon et al., "Cell-free assays for γ-secretase activity," *FASEB J.*, 2000, 14(15):2383-2386.

Mirra et al., "Making the Diagnosis of Alzheimer's Disease—A Primer for Practicing Pathologists," *Arch. Pathol. Lab. Med.*, 1993, 117:132-144.

Mirra et al., "The Consortium to Establish a Registry for Alzheimer's Disease (CERAD)," *Neurology*, 1991, 41:479-486.

Mohs, "Comprehensive and Neuropsychologic Evaluations—The Alzheimer's Disease Assessment Scale," *International Psychogeriatrics*, 1996, 8(2):195-203.

Montine et al., "Increased CSF $F_2$-isoprostane concentration in probable AD," *Neurology*, 1999. 52:562-565.

Murphy et al., "A Simple and Rapid Test of Sensorimotor Function in the Aged Rat," *Neurobiology of Learning and Memory*, 1995, 64:181-186

Murphy et al., "Presenilin 1 Regulates Pharmacologically Distinct γ-Secretase Activities," *J. Biol. Chem.*, 2000, 275(34):26277-26284.

Perez et al., "Mutagenesis Identifies New Signals for β-Amyloid Precursor Protein Endocytosis, Turnover, and the Generation of Secreted Fragments, Including Aβ42," *J. Biol. Chem.*, 1999, 274(27):18851-18856.

Perola et al., "Successful Virtual Screening of a Chemical Database for Farnesyltransferase Inhibitor Leads," *J. Med. Chem.*, 2000, 43:401-408.

Piazza et al., "Antineoplastic Drugs Sulindac Sulfide and Sulfone Inhibit Cell Growth by Inducing Apoptosis," *Cancer Res.*, 1995, 55:3110-3116.

Rick et al., "Short Intertrial Intervals Impair Water Maze Performance in Old Fischer 344 Rats," *J. Gerontol. Biol. Sci.*, 1996, 51A(4):B253-B260.

Riendeau et al., "Comparison of the cyclooxygenase-1 inhibitory properties of nonsteroidal anti-inflammatory drugs (NSAIDs) and selective COX-2 inhibitors, using sensitive microsomal and platelet assays," *Can. J. Physiol. Pharmacol.*, 1997, 75:1088-1095.

Sagi et al., "The Non-cyclooxygenase Targets of Non-steroidal Anti-inflammatory Drugs, Lipoxygenases, Peroxisome Proliferator-activated Receptor, Inhibitor of κB Kinase, and NFκB, Do Not Reduce Amyloid β42 Production," *J. Biol. Chem.*, 2003, 278(34):31825-31830.

Sisodia et al., "Identification and Transport of Full-Length Amyloid Precursor Proteins in Rat Peripheral Nervous System," *J. Neurosci.*, 1993, 13(7):3136-3142.

Smith et al., "Cyclooxygenases: Structural, Cellular, and Molecular Biology," *Annu. Rev. Biochem.*, 2000, 69:145-182.

Sunderland et al., "Longitudinal Stability of CSF Tau Levels in Alzheimer Patients," *Biol. Psychiatry*, 1999, 46:750-755.

Suzuki et al., "An Increased Percentage of Long Amyloid β Protein Secreted by Familial Amyloid β Protein Precursor ($\beta APP_{717}$) Mutants," *Science*, 1994, 264:1336-1340.

Wang et al., "The Profile of Soluble Amyloid β Protein in Cultured Cell Media," *J. Biol. Chem.*, 1996, 271(50):31894-31902.

Weggen et al., "A subset of NSAIDs lower amyloidogenic Aβ42 independently of cyclooxygenase activity," *Nature*, 2001, 414:212-216.

Weggen et al., "Aβ42-lowering Nonsterodial Anti-inflammatory Drugs Preserve intramembrane Cleavage of the Amyloid Precursor Protein (APP) and ErbB-4 Receptor and Signaling through the APP Intracellular Domain," *J. Biol. Chem.*, 2003, 278(33):30748-30754.

Weggen et al., "Evidence That Nonsteroidal Anti-inflammatory Drugs Decrease Amyloid β42 Production by Direct Modulation of γ-Secretase Activity," *J. Biol. Chem.*, 2003, 278(34):31831-31837.

Wiltfang et al., "Improved electrophoretic separation and immunoblotting of beta-amyloid (Aβ) peptides 1-40, 1-42, and 1-43," *Electrophoresis*, 1997, 18:527-532.

Wolfe et al., "A Substrate-Based Difluoro Ketone Selective Inhibits Alzheimer's γ-Secretase Activity," *J. Med. Chem.*, 1998, 41:6-9.

Wolfe et al., "Are Presenilins Intramembrane-Cleaving Proteases? Implications for the Molecular Mechanism of Alzheimer's Disease," *Biochemistry*, 1999, 38(35):11223-11230.

Yuan et al., "Recombinant adenovirus is an appropriate vector for endocytotic protein trafficking studies in cultured neurons," *J. Neurosci. Methods*, 1999, 88:45-54.

Zhang et al., "Malignant Transformation and Antineoplastic Actions of Nonsteroidal Antiinflammatory Drugs (NSAIDs) on Cyclooxygenase-null Embryo Fribroblasts," *J. Exp. Med.*, 1999, 190(4):451-459.

Lee et al., "Regulation of APP Synthesis and Secretion by Neuroimmunophilin Ligands and Cyclooxygenase Inhibitors", *Annals New York Academy of Sciences*, 2000, 920:261-268.

* cited by examiner

RATIO OF
Aβ 1-X/Aβ 1-40

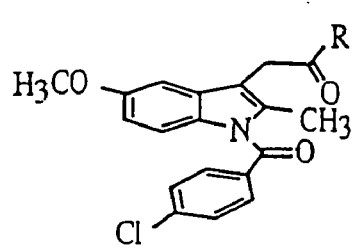
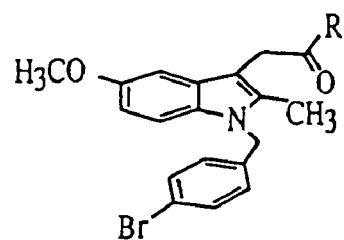

| COMPOUND | R | IC$_{50}$* °COX-1 | hCOX-2 | IC$_{50}$ (COX-1)/ IC$_{50}$ (COX-2)† |
|---|---|---|---|---|
| INDOMETHACIN | OH | 0.050 | 0.75 | 0.070 |
| 4 | HNCH$_3$ | >66 | 0.70 | >90 |
| 5 | OCH$_3$ | 33 | 0.25 | 130 |
| 6 | HN(CH$_2$)$_2$OH | >66 | 0.25 | >287 |
| 7 | HNC$_6$H$_5$(4-NHCOCH$_3$) | >66 | 0.12 | >600 |
| 8 | OC$_6$H$_5$(4-OCH$_3$) | >66 | 0.040 | >1,700 |
| 9 | OC$_6$H$_5$(4-SCH$_3$) | 2.6 | 0.30 | 8.7 |
| 10 | OC$_6$H$_5$(2-SCH$_3$) | >66 | 0.060 | >1,100 |
| 11 | OC$_6$H$_5$(4-F) | 3.0 | 0.075 | 40 |
| 12 | O(3-C$_5$H$_4$N) | 2.5 | 0.050 | 50 |
| 13 | HNC$_6$H$_5$(4-SCH$_3$) | >66 | 0.12 | >600 |
| 14 | HNC$_6$H$_5$(4-F) | >66 | 0.060 | >1,100 |
| 15 | HN(3-C$_5$H$_4$N) | >66 | 0.050 | >1,300 |
| 16 | NC$_5$H$_{10}$ | >66 | >16.5 | — |
| 17 | N(CH$_3$)(CH$_2$)$_2$H$_5$ | >66 | >16.5 | — |
| 18 | NH$_2$ | >20 | 0.70 | >29 |
| 19 | HN(CH$_2$)$_2$C$_6$H$_5$ | >66 | 0.060 | >1,100 |
| 20 | O(CH$_2$)$_2$C$_6$H$_5$ | >66 | 0.050 | >1,320 |
| 21 | ‡ | >66 | >66 | — |
| 22 | ‡ | >66 | >66 | — |
| 23 | ‡ | >66 | 2.5 | >26 |

*IC$_{50}$ VALUES IN µM REPRESENT TIME-DEPENDENT COX INHIBITION AND ARE AVERAGE VALUES FROM DUPLICATE EXPERIMENTS.

†COX-2 SELECTIVITY RATIO.

‡CONTAINS p-BROMOBENZYL GROUP ON THE INDOLE NITROGEN. THE R GROUP IN COMPOUNDS 21, 22, AND 23 ARE PHENETHYL AMIDE, PHENETHYL ESTER, AND FREE ACID, RESPECTIVELY.

FIG. 11-1

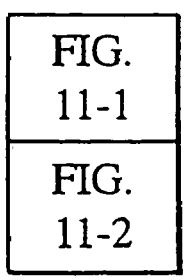

FIG. 11

| COMPOUND | R | IC$_{50}$* oCOX-1 | IC$_{50}$* hCOX-2 | IC$_{50}$ (COX-1)/ IC$_{50}$ (COX-2)† |
|---|---|---|---|---|
| MECLOFENAMIC ACID | OH | 0.040 | 0.050 | 0.72 |
| 24 | HNCH$_3$ | 16.5 | 5.5 | 3.0 |
| 25 | HN(CH$_2$)$_3$Cl | 2.4 | 0.060 | 40 |
| 26 | HN(CH$_2$)$_2$OH | 0.90 | 0.60 | 1.4 |
| 27 | HN(CH$_2$)$_2$OC$_6$H$_5$ | 66 | 0.15 | 440 |
| 28 | HNOCH$_2$C$_6$H$_5$ | 66 | 1.0 | 66 |
| 29 | HNOCH$_2$C$_6$H$_5$(4-NO$_2$) | 60 | 0.20 | 273 |
| 30 | HN(CH$_2$)$_2$C$_6$H$_5$ | 4.0 | 4.5 | 0.90 |
| 31 | HNCH$_2$CO$_2$CH$_3$ | 1.2 | 0.070 | 17 |
| 32 | HNCH$_2$CO$_2$H | 0.30 | 0.40 | 0.75 |

*IC$_{50}$ VALUES IN µM REPRESENT TIME-DEPENDENT COX INHIBITION AND ARE AVERAGE VALUES FROM DUPLICATE EXPERIMENTS.

†COX-2 SELECTIVITY RATIO.

| NO | COMPOUND | STRUCTURE | NO | COMPOUND | STRUCTURE |
|---|---|---|---|---|---|
| 1 | FAUQ-1 | diphenylamine-2-carboxylic acid | 10 | FAUQ-10 | 3'-fluoro derivative |
| 2 | FAUQ-2 | 2'-OCH₃, 4'-NO₂ derivative | 11 | FAUQ-11 | 2'-F, 3'-SO₃H derivative |
| 3 | FAUQ-3 | 2'-NO₂ derivative | 12 | FAUQ-12 | diphenylamine-2-carboxylic acid |
| 4 | FAUQ-4 | diphenylamine-2-carboxylic acid | 13 | FAUQ-13 | 2'-F, 5'-OH derivative |
| 5 | FAUQ-5 | 2'-COOH derivative | 14 | FAUQ-14 | diphenylamine-2-carboxylic acid |
| 6 | FAUQ-6 | 3'-COOH derivative | 15 | FAUQ-15 | 2'-CF₃, 4'-F derivative |
| 7 | FAUQ-7 | 2'-OH derivative | 16 | FAUQ-21 | diphenylamine-2-carboxylic acid |
| 8 | FAUQ-8 | 3'-OH derivative | 17 | FAUQ-17 | 2'-NH-Ac, 4'-SO₃H derivative |
| 9 | FAUQ-20 | 4'-Ac-HN derivative | 18 | FAUQ-18 | 2'-CF₃ derivative |

FIG. 12 ary
Aβ₄₂ LOWERING AGENTS

CROSS REFERENCE TO RELATED APPLICATIONS

This application claims priority to U.S. non-provisional application Ser. No. 10/012,606, filed 7 Dec. 2001, now U.S. Pat. No. 6,911,466, issued Jun. 28, 2005, which is a continuation-in-part of PCT/US2001/11956 filed 12 Apr. 2001, now WO01/78821 A1, which claims benefit from provisional U.S. application Ser. No. 60/196,617, filed 13 Apr. 2000, now expired, all of which are herein incorporated by reference in their entireties.

STATEMENT AS TO FEDERALLY SPONSORED RESEARCH

Funding for the work described herein was provided, in part, by the federal government, which may have certain rights in the invention.

BACKGROUND

1. Technical Field

The invention relates to the use of $A\beta_{42}$ lowering agents to prevent, delay, or reverse the progression of Alzheimer's disease. The invention also relates to methods and materials involved in identifying $A\beta_{42}$ lowering agents that can be used to prevent, delay, or reverse Alzheimer's disease as well as methods and materials involved in identifying agents that (1) increase the risk of developing or (2) hasten the progression of Alzheimer's disease in a mammal.

2. Background Information

Alzheimer's disease (AD) is the most common form of age-related neurodegenerative illness. The defining pathological hallmarks of AD are the presence of neurofibrillary tangles and senile plaques in the brain. Amyloid β polypeptides (Aβ) are the major constituents of amyloid plaques and are derived from altered processing of amyloid precursor proteins (APPs). Aβ consists predominantly of two forms, $A\beta_{40}$ and $A\beta_{42}$. Although $A\beta_{40}$ is the predominant form, recent evidence suggests that $A\beta_{42}$ is the pathogenic form. In addition to $A\beta_{40}$ and $A\beta_{42}$, the processing of APP generates other Aβ forms such as $A\beta_{39}$, $A\beta_{38}$, $A\beta_{37}$, and $A\beta_{34}$.

Genetic predisposition is the largest cause of AD in the population, accounting for perhaps 50% or more cases of this disorder (Blacker et al. (1998) *Arch Neurol* 55:294–6). In the past decade, epidemiological evidence suggests that non-steroidal anti-inflammatory drug (NSAID) treatment, estrogen replacement therapy, and antioxidant therapy may have beneficial effects in AD. Experimental support for these treatment methods, however, is indirect. In addition, there is no convincing evidence from randomized clinical trials that any medication tested to date slows the progression of AD. The rational development of compounds that influence key pathways or targets involved in the development of AD is critically important.

SUMMARY

The invention relates to the use of $A\beta_{42}$ lowering agents to prevent, delay, or reverse the progression of AD. The invention is based on the discovery that some but not all NSAIDs useful for treating AD are those that can selectively reduce the level of the pathogenic $A\beta_{42}$ form, do not affect the level of $A\beta_{40}$, and increase levels of Aβ forms smaller than $A\beta_{40}$ such as $A\beta_{38}$. More specifically, the invention provides methods and materials related to identifying $A\beta_{42}$ lowering agents, including NSAIDs, NSAID derivatives, and NSAID analogues, that (1) can reduce the level of $A\beta_{42}$ by reducing APP processing into $A\beta_{42}$ or by increasing $A\beta_{42}$ catabolism; (2) increase the level of $A\beta_{38}$ by increasing APP processing into Aβ38; and (3) have increased selectivity for reduction of $A\beta_{42}$ relative to inhibition of COX-1, COX-2, or both COX-1 and COX-2. In addition, the invention provides methods and materials related to identifying agents that can increase the risk of developing AD, or hasten the progression of AD, in a mammal. The invention also provides compositions and kits that can be used to prevent, delay, or reverse the progression of AD.

In one embodiment, the invention provides a method of preventing, delaying, or reversing the progression of AD by administering an $A\beta_{42}$ lowering agent to a mammal under conditions in which levels of $A\beta_{42}$ are reduced, levels of $A\beta_{38}$ are increased, and levels of $A\beta_{40}$ are unchanged. The $A\beta_{42}$ lowering agent also can increase the levels of one or more of $A\beta_{34}$, $A\beta_{36}$, $A\beta_{37}$, and $A\beta_{39}$.

The $A\beta_{42}$ lowering agent can be an NSAID, an NSAID derivative, an NSAID analogue, or any compound that reduces levels of $A\beta_{42}$, increases levels of $A\beta_{38}$, and has no effects on levels of $A\beta_{40}$, (i.e., levels of $A\beta_{40}$ are neither increased nor decreased). The $A\beta_{42}$ lowering agent can be an aryl propionic acid derivative, an aryl acetic acid derivative, or an amino carboxylic acid derivative. More specifically, the $A\beta_{42}$ lowering agent can be a structural derivative of an NSAID such as flufenmic acid, meclofenamic acid, fenoprofen, carprofen, ibuprofen, ketoprofen, and flurbiprofen. The $A\beta_{42}$ lowering agent also can be a structural derivative of 5-nitro-2-(3-phenylpropylamino) benzoic acid). Typically, the $A\beta_{42}$ lowering agent either (1) lacks COX-1, COX-2, or both COX-1 and COX-2 inhibiting activity, or (2) has a greater potency for lowering $A\beta_{42}$ levels than for inhibiting COX-1, COX-2, or both COX-1 and COX-2 activity. In one embodiment, the $A\beta_{42}$ lowering agent is R-flurbiprofen.

$A\beta_{42}$ lowering agents of the invention can be used to treat AD in a mammal such as a human. The mammal may not be diagnosed with AD, or may not have a genetic predisposition for AD.

In another embodiment, the invention provides a method for developing an $A\beta_{42}$ lowering agent. The method involves generating derivatives of the NSAIDs meclofenamic acid or flufenamic acid by altering the position of the carboxylic acid group on the phenyl ring or altering the position or type of substituents on the phenyl ring opposite the carboxylic acid group. Derivatives also can be generated by altering the bond connecting the two phenyl rings, altering the carboxylic acid group to propionic acid or another substituent, or performing any combination of these alterations. The derivative is then tested to determine its ability to decrease $A\beta_{42}$ levels while increasing $A\beta_{38}$ levels.

In another embodiment, the invention provides a method for developing an $A\beta_{42}$ lowering agent. The method involves generating derivatives of the NSAIDs fenoprofen, flurbiprofen, or carprofen. Derivatives can be generated by altering the position of the propionic acid group on the phenyl ring, or altering the position or type of substituents on the phenyl ring opposite the propionic acid group. Derivatives also can be generated by altering the bond connecting the two phenyl rings, altering the acetic acid group to carboxylic acid or another substituent, or performing any combination of these alterations. The derivative is then tested to determine its ability to decrease $A\beta_{42}$ levels while increasing $A\beta_{38}$ levels.

In another embodiment, the invention provides a method for developing an $A\beta_{42}$ lowering agent. The method involves generating derivatives of indomethacin by altering the carboxylic acid group to another substituent, altering the indole nitrogen to another substituent, or performing any combination of these alterations. The derivative is then tested to determine its ability to decrease $A\beta_{42}$ levels while increasing $A\beta_{38}$ levels.

In another embodiment, the invention provides a method for developing an $A\beta_{42}$ lowering agent. The method involves generating derivatives of sulindac sulfide by altering the methylthio group, the propionic acid group, or the fluoride moiety to another substituent, or performing any combination of these alterations. The derivative is then tested to determine its ability to decrease $A\beta_{42}$ levels while increasing $A\beta_{38}$ levels.

In another embodiment, the invention provides a method for identifying an $A\beta_{42}$ lowering agent useful for preventing, delaying, or reversing the progression of Alzheimer's disease. The method involves treating a biological composition that has APP and an APP processing activity with a candidate $A\beta_{42}$ lowering agent under conditions in which APP processing occurs. An $A\beta_{42}$ lowering agent, useful for preventing, delaying, or reversing the progression of Alzheimer's disease, is one that, when present, decreases the level of $A\beta_{42}$ in the biological composition.

In another embodiment, the invention provides a method for identifying an $A\beta_{42}$ lowering agent useful for preventing, delaying, or reversing the progression of Alzheimer's disease. The method involves treating a biological composition that has $A\beta_{42}$ and an $A\beta_{42}$ catabolic activity with a candidate $A\beta_{42}$ lowering agent under conditions in which $A\beta_{42}$ catabolism occurs. An $A\beta_{42}$ lowering agent, useful for preventing, delaying, or reversing the progression of Alzheimer's disease, is one that, when present, decreases the level of $A\beta_{42}$ in a biological composition.

In another embodiment, the invention provides a method for identifying an $A\beta_{42}$ lowering agent that has a greater potency for lowering $A\beta_{42}$ levels than for inhibiting COX-1, COX-2, or both COX-1 and COX-2 activity. The method involves identifying $A\beta_{42}$ lowering agents by screening for those having the ability to lower the level of $A\beta_{42}$ in a biological composition. The IC50 of the $A\beta_{42}$ lowering agent for $A\beta_{42}$ lowering can be determined by performing dose response studies. The $A\beta_{42}$ lowering agent is examined for the ability to inhibit COX-1, COX-2, or both COX-1 and COX-2 using in vitro COX-1 and COX-2 inactivation assays. The IC50 for $A\beta_{42}$ lowering is compared to the IC50 for COX-1, COX-2, or both COX-1 and COX-2 inhibition. An $A\beta_{42}$ lowering agent that has an greater potency for lowering $A\beta_{42}$ levels than for inhibiting COX-1, COX-2, or both COX-1 and COX-2 activity is one that has an IC50 for $A\beta_{42}$ lowering greater than ten-fold the IC50 for COX-1, COX-2, or both COX-1 and COX-2 inhibition. The greater potency for lowering $A\beta_{42}$ levels than for inhibiting COX-1, COX-2, or both COX-1 and COX-2 activity can be confirmed by demonstrating that administration of the $A\beta_{42}$ lowering agent to an animal reduces $A\beta_{42}$ levels at doses that do not inhibit or only minimally inhibit COX-1, COX-2, or both COX-1 and COX-2 activity such that significant COX-related side-effects do not occur.

In another embodiment, the invention provides a method for identifying an agent that increases the risk of developing, or hastens progression of, AD in a patient. The method involves exposing a biological composition that has APP and an APP processing activity to a candidate agent under conditions in which APP processing occurs. The level of $A\beta_{42}$ in the biological composition exposed to the candidate agent is compared to the level of $A\beta_{42}$ in a biological composition not exposed to the candidate agent. The candidate agent is one that can increase the risk of developing, or hasten the progression of, AD if an increase in the level of $A\beta_{42}$ in the biological composition exposed to the agent is observed when compared with the level of $A\beta_{42}$ in the biological composition not exposed to the agent.

In another embodiment, the invention provides a method for identifying an agent that increases the risk of developing, or hastens progression of, AD in a patient. The method involves exposing a biological composition that has $A\beta_{42}$ and an $A\beta_{42}$ catabolic activity to a candidate agent under conditions in which $A\beta_{42}$ catabolism occurs. The level of $A\beta_{42}$ in the biological composition exposed to the candidate agent is compared to the level of $A\beta_{42}$ in a biological composition not exposed to the candidate agent. The candidate agent is one that can increase the risk of developing, or hasten the progression of, AD if an increase in the level of $A\beta_{42}$ in the biological composition exposed to the agent is observed when compared with the level of $A\beta_{42}$ in the biological composition not exposed to the agent.

In another embodiment, the invention provides a composition consisting of an $A\beta_{42}$ lowering agent and an antioxidant. The antioxidant can be, without limitation, vitamin E, vitamin C, curcumin, and Gingko biloba.

In another embodiment, the invention provides a composition consisting of an $A\beta_{42}$ lowering agent and a non-selective secretase inhibitor.

In another embodiment, the invention provides a composition consisting of an $A\beta_{42}$ lowering agent and an acetylcholinesterase inhibitor.

In another embodiment, the invention provides kits containing (1) an $A\beta_{42}$ lowering agent and an antioxidant; (2) an $A\beta_{42}$ lowering agent and a non-selective secretase inhibitor; or (3) an $A\beta_{42}$ lowering agent and an acetylcholinesterase inhibitor. Kits can include instructions that indicate dose regimens for the $A\beta_{42}$ lowering agent, the antioxidant, the secretase inhibitor, and/or the acetylcholinesterase inhibitor.

In another embodiment, the invention provides for the use of an $A\beta_{42}$ lowering agent in the manufacture of a medicament for the treatment of AD. When administered to a patient, the medicament containing the $A\beta_{42}$ lowering agent is effective for reducing $A\beta_{42}$ levels without affecting $A\beta_{40}$ levels. The medicament also can increase $A\beta_{38}$ levels, and may also increase $A\beta_{34}$, $A\beta_{36}$, $A\beta_{37}$, or $A\beta_{39}$ levels. The $A\beta_{42}$ lowering agent in the medicament can be an aryl propionic acid derivative, an aryl acetic acid derivative, or an amino carboxylic acid derivative. More specifically, the $A\beta_{42}$ lowering agent in the medicament can be a structural derivative of an NSAID selected from the group consisting of flufenmic acid, meclofenamic acid, fenoprofen, carprofen, ibuprofen, ketoprofen, and flurbiprofen. The $A\beta_{42}$ lowering agent also can be a structural derivative of 5-nitro-2-(3-phenylpropylamino)benzoic acid). The $A\beta_{42}$ lowering agent in the medicament can lack COX-1, COX-2, or both COX-1 and COX-2 inhibiting activity. The $A\beta_{42}$ lowering agent in the medicament can have a greater potency, in vivo, for lowering $A\beta_{42}$ levels than for inhibiting COX-1, COX-2, or both COX-1 and COX-2 activity. The medicament can be used to treat AD in a mammal such as a human. The medicament can be used in a mammal that has not been diagnosed with AD, or in a mammal that does not have a genetic predisposition for AD.

The term "$A\beta_{42}$ lowering agent" as used herein refers to an NSAID, an NSAID derivative, an NSAID analogue, or any compound that (1) has the ability to reduce $A\beta_{42}$ levels, (2) has the ability to increase $A\beta_{38}$ levels, and (3) has no affect on $A\beta_{40}$ levels. The $A\beta_{42}$ lowering agent also can increase the levels of one of $A\beta_{34}$, $A\beta_{36}$, $A\beta_{37}$, or $A\beta_{39}$. The $A\beta_{42}$ lowering agent can be a derivative of aryl propionic acid, aryl acetic acid, or amino carboxylic acid. The $A\beta_{42}$ lowering agent can be a derivative of an NSAID such as flufenmic acid, meclofenamic acid, fenoprofen, carprofen, ibuprofen, ketoprofen, and flurbiprofen. The $A\beta_{42}$ lowering agent can (1) lack COX-1, COX-2, or both COX-1 and COX-2 inhibiting activity; or (2) have a much greater potency, in vivo, for lowering $A\beta_{42}$ relative to COX-1, COX-2, or both COX-1 and COX-2 inhibiting activity.

As used herein, the terms "increase" and "decrease," refer to a change in any amount that is reproducible and significant. A reproducible and significant change is differentiated from irreproducible or insignificant experimental variations in measurements by standard statistical analysis methods including analysis that involves comparison with changes observed for control agents known to have no effects on the levels of the $A\beta$ forms of interest. A significant change can be any amount such as a 0.5, 1, 5, 10, 20, 40 or more than 40% increase or decrease.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 12 is a compilation of the structures of newly synthesized biphenyl amines.

DETAILED DESCRIPTION

Figure 1:
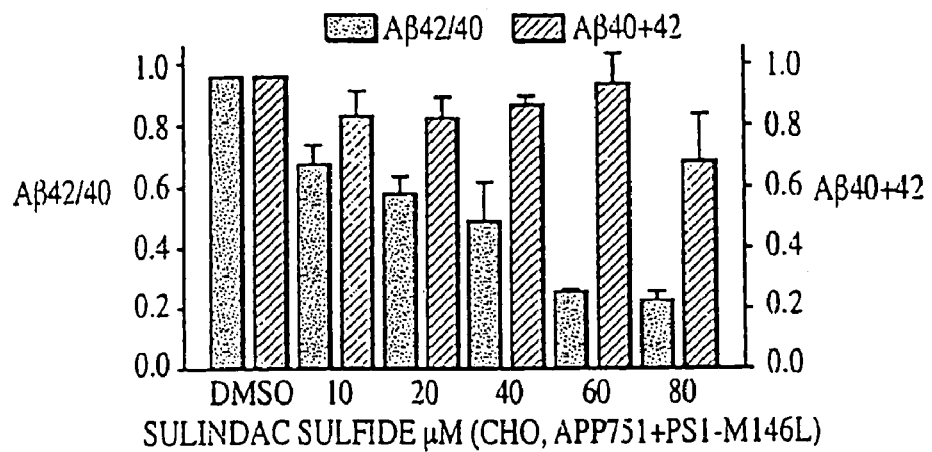
FIG. 1 is a bar graph summarizing $A\beta_{42}/A\beta_{40}$ ratios and total $A\beta$ levels determined for CHO cells expressing APP751 and PS-1 mutant M146L that had been treated with DMSO or with various concentrations of sulindac sulfide.

The invention relates to the use of $A\beta_{42}$ lowering agents to prevent, delay, or reverse the progression of AD. The invention is based on the discovery that some but not all NSAIDs useful for treating AD are those that can reduce the level of the pathogenic $A\beta_{42}$ form and increase the levels of $A\beta$ forms smaller than $A\beta_{40}$ such as $A\beta_{38}$. Therefore, the invention provides methods and materials related to identifying $A\beta_{42}$ lowering agents, including NSAIDs, NSAID derivatives, and NSAID analogues that (1) can reduce the level of $A\beta_{42}$ by reducing APP processing into $A\beta_{42}$ or by increasing $A\beta_{42}$ catabolism; (2) increase the level of $A\beta_{38}$ by increasing APP processing into $A\beta_{38}$; and (3) have increased selectivity for reduction of $A\beta_{42}$ relative to inhibition of COX-1, COX-2, or both COX-1 and COX-2. In addition, the invention provides methods and materials related to identifying agents that can increase the risk of, or hasten the progression of, AD in a mammal, by increasing the processing of APP into $A\beta_{42}$, or decreasing the catabolism of $A\beta_{42}$. The invention also provides compositions and kits that can be used to prevent, delay, or reverse the progression of AD.

1. $A\beta_{42}$ Lowering Agents $A\beta_{42}$ lowering agents include, without limitation, NSAIDs, NSAID derivatives, and NSAID analogues. NSAIDs can be FDA-approved NSAIDs. NSAID derivatives are compounds generated by modifying functional groups of known NSAIDs. Once modified, derivatives may or may not have the anti-inflammatory properties of the parent NSAIDs. Structural analogues of NSAIDs are compounds that are structurally similar to NSAIDs. Analogues also may not have the anti-inflammatory properties of the corresponding structurally similar NSAIDs to which they resemble.

NSAIDs are non-steroidal anti-inflammatory drugs that are distinct from steroidal drugs with anti-inflammatory properties such as corticosteroids. NSAIDs, many of which are organic acids, typically have analgesic (pain-killing), anti-inflammatory, and antipyretic (fever-reducing) properties. Some examples of NSAIDs include salicylic acid (Aspirin), ibuprofen (Motrin, Advil), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), Meclofenamic acid (Meclofen) and indomethacin (Indocin). NSAIDs can be grouped into classes, for example, amino aryl carboxylic acid derivatives (e.g., flufenamic acid, meclofenamic acid); aryl acetic acid derivatives (e.g., indomethacin, sulindac); and aryl propionic acid derivatives (fenoprofen, ibuprofen, carprofen).

Although NSAIDs have multiple cellular effects (see Cronstein et al. (1995) *Annu Rev Pharmacol Toxicol* 35:449–62; and Amin et al. (1999) *Cell Mol Life Sci* 56:305–12), many act through direct inhibition of COX enzymes. COX enzymes oxidize arachidonic acids from membrane bound phospholipids to prostaglandins (see Smith et al. (2000) *Ann Rev Biochem* 69:145–82). Inhibition of COX enzymes and therefore prostaglandin synthesis is believed to underlie the analgesic and anti-inflammatory properties of aspirin and NSAIDs (see Dubois et al. (1998) *FASEB J* 12:1063–73). There are two isoforms of COX: COX-1 and COX-2. Although COX-1 and COX-2 catalyze the same reaction, they are derived from two different genes. COX-1 is traditionally viewed as a constitutive or housekeeping enzyme while COX-2 is viewed as an inducible enzyme that is expressed during inflammatory circumstances. COX products, primarily prostaglandin E2, modulate classical signs of inflammation. Another COX product is thromboxane A2 that promotes platelet aggregation and vasoconstriction. Although COX is expressed in neurons, its function in the central nervous system is unclear.

Another target of NSAIDs is the peroxisome proliferator-activator receptor (PPAR) family of nuclear hormone receptors. The PPAR family consists of at least three subtypes: PPARα, PPARδ, and PPARγ (see Corton et al. (2000) *Annu Rev Pharmacol Toxicol* 40:491–518). These receptors are thought to function as ligand-dependent activators of transcription. All three PPAR members are modulated by NSAIDs, although in different ways. For example, NSAIDs activate the activities of PPARδ and PPARγ but inhibit PPARγ activity (see He et al. (1999) *Cell* 99:335–45). It is known that PPARγ expression is increased in brains of AD individuals (Kitamura et al. (1999) *Biochem Biophys Res Commun* 254:582–6), and that PPARγ agonists block Aβ-stimulated secretion of proinflammatory products of microglia, including IL-1 and TNF-α (see Combs et al. (2000) *J Neurosci* 20:558–67). It has been suggested that the beneficial effects of NSAIDs in AD may be mediated via their activity on PPARγ rather than or in addition to COX inhibition (Combs et al. (2000) *J Neurosci* 20:558–67). It is not known, however, what downstream genes are activated by PPARs, or whether they are involved in Aβ production.

An $A\beta_{42}$ lowering agent is any compound that has the following three properties: (1) the ability to reduce the level of $A\beta_{42}$ either through reducing APP processing or increasing $A\beta_{42}$ catabolism, (2) no effect on the level of $A\beta_{40}$, and (3) and the ability to increase $A\beta_{38}$. These three properties differentiate $A\beta_{42}$ lowering agents of the invention from other compounds having COX inhibiting activities or those that do not selectively reduce $A\beta_{42}$ production. These three properties are referred to collectively as the Alzheimer's-$A\beta_{42}$-NSAID ($A\beta_{42}$-NSAID) footprint. In addition to having the $A\beta_{42}$-NSAID footprint, an $A\beta_{42}$ lowering agent of the invention can modulate the level of Aβ forms smaller than $A\beta_{40}$ such as $A\beta_{34}$, $A\beta_{36}$, $A\beta_{37}$, and $A\beta_{39}$.

2. Identification of $A\beta_{42}$ Lowering Agents Useful for Treating AD $A\beta_{42}$ lowering agents can be identified from collections of NSAIDs, NSAID derivatives, NSAID analogues, or other compounds using the $A\beta_{42}$-NSAID footprint. Such compounds can be obtained from any commercial source. For example, NSAIDs, NSAID derivatives, and NSAID analogues can be obtained from Sigma, Biomol, Cayman Chemical, ICN, or from the web through the Chemnavigator website. Novel NSAIDs, novel NSAID derivatives, and novel NSAID analogues can be chemically synthesized using methods described in many published protocols. NSAIDs, NSAID derivatives, and NSAID analogues can be synthesized with altered potency for their known targets such as COX-1 and COX-2. For example Kalgutkar et al. (2000) PNAS 97:925–930 have made derivatives of indomethacin and meclofenamic acid and Bayly et al (1999) *Biorg and Med Chem Letters* 9:307–312 have made derivatives of Flurbiprofen. Indeed, because of the effort to engineer NSAIDs so that they preferentially inhibit COX-2 rather than non-selectively inhibit COX-1 and COX-2, there are dozens of published reports documenting synthesis of novel derivatives of known NSAIDs (reviewed in Dewitt (1999) Molecular Pharmacology 55:625–631).

It is recognized that some NSAID derivatives or NSAID analogues generated can have (1) increased potency for lowering $A\beta_{42}$ levels and (2) decreased potency for COX inhibition. Although derivatives and analogues may no longer be considered NSAIDs since they may lack anti-inflammatory properties, $A\beta_{42}$ lowering agents can include such NSAID derivatives and NSAID analogues.

$A\beta_{42}$ lowering agents that have the $A\beta_{42}$-NSAID footprint can be identified using cell free assays, in vitro cell-based assays, and in vivo animal studies. $A\beta_{42}$ lowering agents can be dissolved in any suitable vehicle for in vitro cell culture studies or in vivo animal or human studies. A vehicle is an inert solvent in which a compound can be dissolved for administration. It is recognized that for any given $A\beta_{42}$ lowering agent, a vehicle suitable for in vitro cell culture studies or in vivo animal studies may not be the same as the vehicle used for human treatment. Some examples of suitable vehicles for cell culture or animal studies include water, dimethyl sulfoxide, ethanol, and ethyl acetate.

To identify $A\beta_{42}$ lowering agents that reduce APP processing, a biological composition having an APP processing activity (i.e. an activity that processes APP into various Aβ forms, one of which is $A\beta_{42}$), is incubated with APP under conditions in which APP processing occurs. To identify $A\beta_{42}$ lowering agents that increase $A\beta_{42}$ catabolism, a biological composition having $A\beta_{42}$ catabolic activity is incubated with $A\beta_{42}$ under conditions in which $A\beta_{42}$ catabolism occurs. Depending on the nature of the biological composition, the APP or $A\beta_{42}$ substrate can be added to the biological composition, or, each or both can be a component of the biological composition. APP processing or $A\beta_{42}$ catabolism is allowed to take place in the presence or absence of the candidate $A\beta_{42}$ lowering agent. The level of $A\beta_{42}$ generated from APP processing or the level of $A\beta_{42}$ remaining after the catabolic reaction, in the presence and absence of the candidate $A\beta_{42}$ lowering agent, is determined and compared. $A\beta_{42}$ lowering agents useful for treating AD are those that reduce the level of $A\beta_{42}$ either by reducing APP processing into $A\beta_{42}$ or by enhancing $A\beta_{42}$ catabolism and increasing $A\beta_{38}$ production.

The biological composition having an APP processing and/or catabolic activity can be a cell-free biological sample. For example, a cell-free biological sample can be a purified or partially purified enzyme preparation; it also can be a cell lysate generated from cells able to process APP into $A\beta_{42}$ or from cells able to catabolize $A\beta_{42}$. Cell lysates can be prepared using known methods such as, for example, sonication or detergent-based lysis. In the case of an enzyme preparation or cell lysate, APP can be added to the biological composition having the APP processing activity, or $A\beta_{42}$ can be added to the biological composition having $A\beta_{42}$ catabolic activity.

In addition, the biological composition can be any mammalian cell that has an APP processing activity as well as a nucleic acid vector encoding APP. Alternatively, the biological composition can be any mammalian cell that has $A\beta$ catabolic activity as well as a nucleic acid vector or a viral nucleic acid-based vector containing a gene that encodes $A\beta_{42}$. The vector typically is an autonomously replicating molecule, a molecule that does not replicate but is transiently transfected into the mammalian cell, or a vector that is integrated into the genome of the cell. Typically, the mammalian cell is any cell that can be used for heterologous expression of the vector-encoded APP or $A\beta_{42}$ in tissue culture. For example, the mammalian cell can be a Chinese hamster ovary (CHO) cell, a fibroblast cell, or a human neuroglioma cell. The mammalian cell also can be one that naturally produces APP and processes it into $A\beta_{42}$, or one that naturally produces and catabolizes $A\beta_{42}$.

Further, the biological composition can be an animal such as a transgenic mouse that is engineered to over-express a form of APP that then is processed into $A\beta_{42}$. Alternatively, the animal can be a transgenic mouse that is engineered to over-express $A\beta_{42}$. Animals can be, for example, rodents such as mice, rats, hamsters, and gerbils. Animals also can be rabbits, dogs, cats, pigs, and non-human primates, for example, monkeys.

To perform an in vitro cell-free assay, a cell-free biological sample having an activity that can process APP into $A\beta_{42}$ is incubated with the substrate APP under conditions in which APP is processed into various $A\beta$ forms including $A\beta_{42}$ (see Mclendon et al. (2000) FASEB 14:2383–2386). Alternatively, a cell-free biological sample having an activity that can catabolize $A\beta_{42}$ is incubated with the substrate $A\beta_{42}$ under conditions in which $A\beta_{42}$ is catabolized. To determine whether a candidate $A\beta_{42}$ lowering agent has an effect on the processing of APP into $A\beta_{42}$ or the catabolism of $A\beta_{42}$, two reactions are compared. In one reaction, the candidate $A\beta_{42}$ lowering agent is included in the processing or catabolic reaction, while in a second reaction, the candidate $A\beta_{42}$ lowering agent is not included in the processing or catabolic reaction. Levels of the different $A\beta$ forms produced in the reaction containing the candidate $A\beta_{42}$ lowering agent are compared with levels of the different $A\beta$ forms produced in the reaction that does not contain the candidate $A\beta_{42}$ lowering agent.

The different $A\beta$ forms can be detected using any standard antibody based assays such as, for example, immunoprecipitation, western hybridization, and sandwich enzyme-linked immunosorbent assays (ELISA). Different $A\beta$ forms also can be detected by mass spectrometry; see, for example, Wang et al. (1996) *J Biol Chem* 271:31894–902. Levels of $A\beta$ species can be quantified using known methods. For example, internal standards can be used as well as calibration curves generated by performing the assay with known amounts of standards.

In vitro cell-based assays can be used determine whether a candidate $A\beta_{42}$ lowering agent has an effect on the processing of APP into $A\beta_{42}$ or an effect on catabolism of $A\beta_{42}$. Typically, cell cultures are treated with a candidate $A\beta_{42}$ lowering agent. Then the level of $A\beta_{42}$ in cultures treated with a candidate $A\beta_{42}$ lowering agent is compared with the level of $A\beta_{42}$ in untreated cultures. For example, mammalian cells expressing APP are incubated under conditions that allow for APP expression and processing as well as $A\beta_{42}$ secretion into the cell supernatant. The level of $A\beta_{42}$ in this culture is compared with the level of $A\beta_{42}$ in a similarly incubated culture that has been treated with the candidate $A\beta_{42}$ lowering agent. Alternatively, mammalian cells expressing $A\beta_{42}$ are incubated under conditions that allow for $A\beta_{42}$ catabolism. The level of $A\beta_{42}$ in this culture is compared with the level of $A\beta_{42}$ in a similar culture that has been treated with the candidate $A\beta_{42}$ lowering agent.

In vivo animal studies also can be used to identify $A\beta_{42}$ lowering agents useful for treating AD. Typically, animals are treated with a candidate $A\beta_{42}$ lowering agent and the levels of $A\beta_{42}$ in plasma, CSF, and/or brain are compared between treated animals and those untreated. The candidate $A\beta_{42}$ lowering agent can be administered to animals in various ways. For example, the candidate $A\beta_{42}$ lowering agent can be dissolved in a suitable vehicle and administered directly using a medicine dropper or by injection. The candidate $A\beta_{42}$ lowering agent also can be administered as a component of drinking water or feed. Levels of $A\beta$ in plasma, cerebral spinal fluid (CSF), and brain are determined using known methods. For example, levels of $A\beta_{42}$ can be determined using sandwich ELISA or mass spectrometry in combination with internal standards or a calibration curve. Plasma and CSF can be obtained from an animal using standard methods. For example, plasma can be obtained from blood by centrifugation, CSF can be isolated using standard methods, and brain tissue can be obtained from sacrificed animals.

When present in an in vitro or in vivo APP processing or $A\beta_{42}$ catabolic reaction, $A\beta_{42}$ lowering agents reduce the level of $A\beta_{42}$ generated by APP processing or remaining following $A\beta$ catabolism. For example, in an in vitro cell-free assay, the level of $A\beta_{42}$ is reduced due to either a reduction of APP processing or an increase in $A\beta_{42}$ catabolism in the presence the $A\beta_{42}$ lowering agent. In an in vitro cell culture study, a reduction in the level of $A\beta_{42}$ secreted into the supernatant results from the effect of the $A\beta_{42}$ lowering agent on either a reduction in processing of APP into $A\beta_{42}$ or an increased catabolism of $A\beta_{42}$. Similarly, in animal studies, a reduction in the level of $A\beta_{42}$ that can be detected in plasma, CSF, or brain is attributed to the effect of the $A\beta_{42}$ lowering agent on either a reduction in the processing of APP into $A\beta_{42}$ or an increase in the catabolism of $A\beta_{42}$.

The level of $A\beta_{42}$ can be reduced by a detectable amount. For example, treatment with an $A\beta_{42}$ lowering agent leads to a 0.5, 1, 3, 5, 7, 15, 20, 40, 50, or more than 50% reduction in the level of $A\beta_{42}$ generated by APP processing or remaining following $A\beta_{42}$ catabolism when compared with that in the absence of the $A\beta_{42}$ lowering agent. Preferably, treatment with the $A\beta_{42}$ lowering agent leads to at least a 20% reduction in the level of $A\beta_{42}$ generated when compared to that in the absence of $A\beta_{42}$ lowering agent. More preferably, treatment with an $A\beta_{42}$ lowering agent leads to at least a 40% reduction the level of $A\beta_{42}$ when compared to that in the absence of an $A\beta_{42}$ lowering agent.

Typically, the $A\beta_{42}$ lowering agent-associated reduction of $A\beta_{42}$ levels is accompanied by an increase in the level of Aβ$_{38}$. In contrast, no change is observed in (1) the level of Aβ$_{40}$ generated by APP processing or Aβ$_{42}$ catabolism in cell-free assays, (2) the level of Aβ$_{40}$ secretion into culture supernatants in cell-based assays, or (3) the level of Aβ$_{40}$ detected in blood plasma, CSF, or brains of animals treated with Aβ$_{42}$ lowering agent.

Aβ$_{42}$ lowering agents of the invention may lack COX inhibitory activity or have reduced COX-1, COX-2, or both COX-1 and COX-2 activity. COX inhibitory activity can be determined using known methods. For example, COX inhibitory activity can be determined using the method described in Kalgutkar et al. (2000) *PNAS* 97:925–930.

A method to identify NSAID derivatives and NSAID analogues that possess Aβ$_{42}$ lowering ability and have altered COX activity is described. NSAID derivatives and NSAID analogues of aminocarboxylic acids, arylacetic acids and arylpoprionic acids can be tested for their ability to lower Aβ$_{42}$ and increase Aβ$_{38}$ in cultured cells and in animals (as described herein). They also can be tested simultaneously for their ability to inactivate COX-1 and COX-2 using in vitro assays as described by Kalgutkar et al. (2000) *PNAS* 97:925–930. Derivatives of the NSAIDs sulindac, meclofenamic acid, flufenamic acid, indomethacin, carprofen, fenoprofen, and flurbiprofen that can be tested include the following:

(1) meclofenamic acid and flufenamic acid derivatives in which (a) the position of the carboxylic acid substituent on the phenyl ring is altered, (b) the position or type of substituents on the phenyl ring opposite the caraboxylic acid substituent are altered, (c) the bond connecting the two phenyl rings is altered, (d) the carboxylic acid substituent is altered to a propionic acid or other derivative, or (e) any combination of these alterations;

(2) fenoprofen, flurbiprofen, and carprofen derivatives in which (a) the position of the propionic acid substituent on the phenyl ring is altered, (b) the position or type of substituents on the phenyl ring opposite the propionic acid substituent is altered, (c) the bond connecting the two phenyl rings is altered, (d) the acetic acid substituent is altered to a carboxylic acid or other derivative, or (e) any combination of these alterations;

(3) indomethacin derivatives in which (a) the carboxylic acid group on indomethacin is altered to other substituents, (b) the substituent on the indole nitrogen is altered, or (c) any combination of the two;

(4) sulindac sulfide in which (a) the methylthio derivative of sulindac sulfide is altered to other substituents, (b) the propionic acid derivative is altered to other substituents, (c) the Fluoride is altered to other substituents, or (d) any combination of the above.

In addition structural analogues of NSAIDs that possess Aβ$_{42}$ lowering ability, identified by pharamacophore searches (Perola et al., (2000) *J. Med Chem*.43: 401–408) or other computer based structural comparison programs of commercially available compounds can be tested for Aβ$_{42}$ lowering activity, ability to increase Aβ$_{38}$, and COX inhibition as described herein.

3. Identification of Mammals in need of Treatment with an Aβ$_{42}$ Lowering Agent Clinical symptoms of AD include, for example, progressive disorientation, memory loss, and aphasia; eventually, disablement, muteness, and immobility occur. Pathological indicators of AD include, for example, the presence of neurofibrillary tangles, neuritic plaques, and amyloid angiopathy. Preventing the progression of AD can be interpreted to mean preventing the onset or further development of clinical symptoms and/or pathological indicators of AD. For example, an individual who does not have clinical symptoms or pathological indicators of AD can be prevented from developing clinical symptoms or pathological indicators. Further, an individual who has a mild form of AD can be prevented from developing a more severe form of AD. Delaying the progression of AD can be interpreted to mean delaying the time of onset of AD-related symptoms and/or pathological indicators or slowing the rate of progression of AD, determined by the rate of development of clinical symptoms and pathological indicators. Reversing the progression of AD can be interpreted to mean that the severity of an AD condition has been lessened, i.e., the AD condition of an individual has changed from severe to less severe as indicated by fewer clinical symptoms or pathological indicators.

An individual can choose to take an Aβ$_{42}$ lowering agent as a preventative measure to avoid developing AD. For example, an individual with a genetic predisposition to AD can take an Aβ$_{42}$ lowering agent to prevent or delay the development of AD. A genetic predisposition can be determined based on known methods. For example, an individual can be considered to have a genetic predisposition to AD if the individual has a family history of AD. Genetic predisposition to AD also can include point mutations in certain genes such as the APP gene, the presenilin-1 or presenilin-2 gene, or the apolipoprotein E gene. Such mutations can predispose individuals to early-onset familial AD (FAD), increased risk of developing AD, or decreased age at onset of AD. (See page 1332, Table 30-2 of Cotran et al. (1999) *Robbins Pathologic Basis of Disease*, Sixth Edition, W. B. Saunders Company; and U.S. Pat. No. 5,455,169.) Furthermore, an individual who has clinical symptoms of, or has been diagnosed with, AD can take an Aβ$_{42}$ lowering agent to prevent or delay further progression of AD as well as to reverse the pathological condition of the disease.

An AD diagnosis can be made using any known method. Typically, AD is diagnosed using a combination of clinical and pathological assessments. For example, progression or severity of AD can be determined using Mini Mental State Examination (MMSE) as described by Mohs et al. (1996) *Int Psychogeriatr* 8:195–203; Alzheimer's Disease Assessment Scale-cognitive component (ADAS-cog) as described by Galasko et al. (1997) *Alzheimer Dis Assoc Disord*, 11 suppl 2:S33-9; the Alzheimer's Disease Cooperative Study Activities of Daily Living scale (ADCS-ADL) as described by McKhann et al. (1984) *Neurology* 34:939–944; and the NINCDS-ADRDA criteria as described by Folstein et al. (1975) *J Psychiatr Res* 12:189–198. In addition, methods that allow for evaluating different regions of the brain and estimating plaque and tangle frequencies can be used. These methods are described by Braak et al. (1991) *Acta Neuropathol* 82:239–259; Khachaturian (1985) *Arch Neuro* 42:1097–1105; Mirra et al. (1991) *Neurology* 41:479–486; and Mirra et al. (1993) *Arch Pathol Lab Med* 117:132–144.

4. Treatment of Mammals with Aβ$_{42}$ Lowering Agents

Aβ$_{42}$ lowering agents can be administered in any standard form using any standard method. For example, Aβ$_{42}$ lowering agents can be in the form of tablets or capsules that are taken orally. Aβ$_{42}$ lowering agents also can be in a liquid form that can be taken orally or by injection. Aβ$_{42}$ lowering agents also can be in the form of suppositories. Further, $A\beta_{42}$ lowering agents can be in the form of creams, gels, and foams that can be applied to the skin, or in the form of an inhalant.

$A\beta_{42}$ lowering agents can be administered at any dose that is sufficient to reduce levels of $A\beta_{42}$ in the blood plasma, CSF, or brain. Lower doses can be taken over a period of years to prevent and/or delay the progression of AD. Higher doses can be taken to reverse the progression of AD. Depending on the effectiveness and toxicity of a particular $A\beta_{42}$ lowering agent, an $A\beta_{42}$ lowering agent can be used at a dose of 0.1–50 mg/kg/day.

5. Compositions and Kits

The invention also provides pharmaceutical compositions containing combinations of an $A\beta_{42}$ lowering agent and an antioxidant effective in preventing, delaying, or reversing the progression of Alzheimer's disease. An $A\beta_{42}$ lowering agent of the invention that has the ability to reduce $A\beta_{42}$ levels can be combined with any antioxidant. The antioxidant can be a vitamin, for example vitamin E, vitamin C or curcumin; the antioxidant also can be Gingko biloba. Other pharmaceutical compositions can include an $A\beta_{42}$ lowering agent and a non-selective secretase inhibitor or an acetylcholinesterase inhibitor.

The pharmaceutical composition can be in any form, for example tablets, capsules, liquids, creams, gels, or suppositories and can include a suitable pharmaceutical carrier. In addition, the invention provides kits containing pharmaceutical compositions of $A\beta_{42}$ lowering agents and antioxidants as well as instructions that indicate dose regimens for effective use.

The invention will be further described in the following examples, which do not limit the scope of the invention described in the claims.

EXAMPLES

Example 1

Cell Cultures, Drug Treatments, and Cell Toxicity Analysis

Cell cultures were maintained in standard cell culture media supplemented with 10% fetal bovine serum and 100 U/mL penicillin/streptomycin (Life Technologies Inc., Germany). Cell cultures consisted of the following: Chinese hamster ovary (CHO) cells that expressed human APP751 from a vector containing a gene encoding APP751; CHO cells that expressed both human APP751 and human mutant PS-1 (M146L) from vectors containing genes encoding APP751 and mutant PS-1 (M146L); CHO cells that expressed human mutant APP751 (V717F) from a vector containing a gene encoding mutant APP751 (V717F); human neuroglioma cells HS683 that expressed human wild type APP695 from a vector containing a gene encoding wild type APP695; HEK 293 cells that expressed human wild type APP695 from a vector containing a gene encoding wild type APP695; and embryonic fibroblasts (that had immortalized spontaneously) from COX-1 and COX-2 double-knockout mice.

The NSAIDs, sulindac sulfide (50 mM, Biomol, Pa., USA), sulindac sulfone (50 mM, Biomol, Pa., USA), naproxen (100 mM, Cayman Chemical, MI, USA), and aspirin (2.5 M, ICN Biomedicals, Calif., USA) were dissolved in the vehicle DMSO. Indomethacin (50 mM, Biomol, Pa., USA) and (S)-ibuprofen (250 mM, Biomol, Pa., USA) were dissolved in ethanol. Celecoxib and rofecoxib capsules were obtained from and dissolved in ethyl acetate. For analyses of $A\beta$ secretion, APP processing, and notch cleavage, cells were cultured in serum-containing media and pretreated overnight with a specific NSAID. The next day, media were changed and cultures were treated with the same NSAID for another 24 hours.

NSAID toxicity in CHO or HS683 cells was examined using standard MTT-assay (3-(4,5-Dimethyl-2-thiazolylyl)-2,5-diphenyl-2H-tetrazolium Bromide) or [$^3$H]-thymidine incorporation assay. For cell toxicity studies, cells were treated with sulindac sulfide at concentrations up to 100 μM, indomethacin at concentrations up to 200 μM, and ibuprofen at concentrations up to 1 mM.

Example 2

Antibodies

Antibodies used included the following: 5A3 and 1G7, two monoclonal antibodies that recognized non-overlapping epitopes between residues 380–665 of APP; CT15, a polyclonal antibody that recognized the C-terminal fifteen amino acid residues of APP; 26D6, a monoclonal antibody that recognized amino acid residues 1–12 of the $A\beta$ sequence; 9E10, a monoclonal antibody that recognized the myc-epitope sequence; anti-COX-2 antibody, a monoclonal antibody that recognized COX-2; and M-20, a polyclonal antibody that recognized COX-1. The antibodies 5A3, 1G7, CT15, and 26D6 were described by Koo et al. (1996) *J Cell Sci* 109:991–8; Sisodia et al. (1993) *J Neurosci* 13:3136–42; and Lu et al. (2000) *Nat Med* 6:397–404. The monoclonal antibody 9E10 was purchased from Calbiochem-Novobiochem, Calif., USA. The monoclonal anti-COX-2 antibody was purchased from BD Transduction Laboratories, Calif., USA. The polyclonal antibody M-20 was purchased from Santa Cruz Biotechnology, Calif., USA.

Example 3

ELISA $A\beta$ was detected by sandwich enzyme-linked immunosorbent assay (ELISA) as described by Murphy et al. (2000) *J Biol Chem* 275:26277–84. Following NSAID treatment, culture supernatants were collected, and cell debris was removed by centrifugation. Complete protease inhibitor cocktail (Roche Molecular Biochemicals, IN, USA) was added to the media and $A\beta_{40}$ and $A\beta_{42}$ levels were quantified using end-specific $A\beta$ ELISAs. All measurements were performed in duplicate.

Example 4

Adenoviral Infection of Embryonic Fibroblasts Derived from COX-1/COX-2 Double-knockout Mice The adenoviral vector containing a gene encoding APP695 was described by Yuan et al. (1999) *J Neurosci Methods* 88:45–54. Primary fibroblasts derived from COX-1/COX-2 double-knockout mice were infected with 100 plaque-forming units (PFU) of viral vector per cell. Infection was performed in serum-free medium for two hours. Medium was changed and cells were treated with NSAIDs as described in Example 1.

Example 5

Analyses of APP and Notch Processing

Expression of holo-APP and APP C-terminal fragments (CTFs) was examined by Western blot analysis using antibody CT-15. APP secretion was examined by Western blotting using a mixture of 5A3/IG7 antibodies. APP turnover was examined by pulse labeling of CHO cells with 150 µCi [$^{35}$S]-methionine for fifteen minutes followed by a cold chase step for up to four hours. Cell lysates were immunoprecipitated with antibody CT-15, subjected to SDS-PAGE, and analyzed by phosphor imaging.

APP surface expression and internalization were measured as described by Koo et al. (1996) *J Cell Sci* 109:991–8. Iodinated antibody 1G7, at approximately 3–6 µCi/µg, was applied to confluent layers of CHO cells in binding medium (DMEM, 0.2% BSA, 20 mM HEPES [pH 7.4]) and incubated at 37° C. for thirty minutes. After incubation, cells were rapidly chilled on ice and the reaction was quenched by the addition of ice-cold binding medium. To remove unbound antibody, chilled cells were washed multiple times with ice-cold Dulbecco's phosphate-buffered saline (Life Technologies Inc.). Antibody bound to cell surface APP was detached by washing with ice-cold PBS (pH 2) for five minutes; this constituted the acid-labile APP antibody pool. Cells were lysed in 0.2 M NaOH; lysates contained the acid-resistant APP antibody pool. Acid-labile and acid-resistant APP antibody counts were measured by γ counting. The ratio of acid-resistant to acid-labile count was a measure of the internalized to the cell surface APP pool.

Two Notch-encoding vector constructs were used in examining Notch processing. These were a construct expressing a myc-tagged NH$_2$-terminal truncated Notch-1 polypeptide (NotchΔEMV), and a construct expressing only the Notch intracellular cytoplasmic domain (NICD) (see Kopan et al. (1996) *Proc Natl Acad Sci USA* 93:1683–8). In the construct expressing a myc-tagged NH$_2$-terminal truncated Notch-1 polypeptide, the start codon, a methionine at position 1726, was mutated to a valine to eliminate translation initiation.

Example 6

Mass Spectrometry

Secretion of Aβ peptides was analyzed using immunoprecipitation/mass spectrometry as described by Wang et al. (1996) *J Biol Chem* 271:31894–902. Briefly, 1 mL amount of culture supernatant was subjected to immunoprecipitation using the monoclonal antibody 4G8 (Senetek, Calif., USA). Molecular masses and concentrations of Aβ peptides were measured using a matrix assisted laser desorption/ionization time-of-flight (MALDI-TOF) mass spectrometer. To compare the concentrations of individual Aβ species in culture supernatants, synthetic Aβ$_{1228}$ peptides (Sigma, Mo., USA) were added to the supernatant samples as internal standards and relative peak heights were calculated.

Example 7

Bicine/Urea Aβ Western Blot Analysis

Bicine/Urea Aβ western blot analysis was performed as described by Wiltfang et al. (1997) *Electrophoresis* 18:527–32. A 1 mL amount of culture supernatant was subjected to immunoprecipitation using monoclonal antibody 26D6. Immunoprecipitates were mixed with sample buffer and heated to 95° C. for five minutes. Eluant samples were separated on Bicine/Urea gels, then transferred to nitrocellulose membranes, and probed with antibody 26D6. Standard Aβ$_{1-40}$, Aβ$_{1-42}$ and Aβ$_{1-38}$ peptides (Sigma, Mo., USA) were used for identification of the Aβ species.

Example 8

Figure 2:
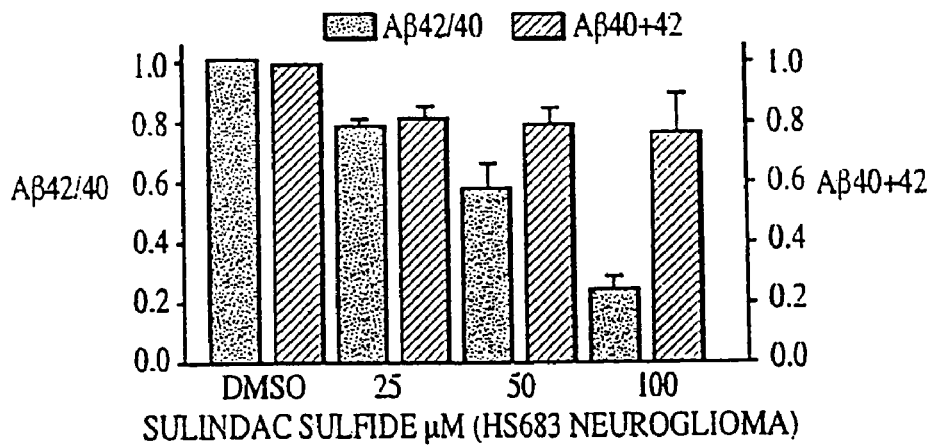
FIG. 2 is a bar graph summarizing $A\beta_{42}/A\beta_{40}$ ratios and total $A\beta$ levels determined for human neuroglioma cells (HS683) expressing APP695 that had been treated with DMSO or with various concentrations of sulindac sulfide.

Cells Treated with the Non-Selective COX-Inhibitor Sulindac Sulfide Showed Reductions in Levels of Aβ42 Secretions Cell cultures were treated with increasing concentrations of the NSAID sulindac sulfide. Levels of Aβ$_{40}$ and Aβ$_{42}$ in culture supernatants were analyzed using ELISA. FIG. 1 is a graph comparing the Aβ$_{42}$/Aβ$_{40}$ ratios of sulindac sulfide-treated CHO cell cultures expressing APP751 and the PS-1 mutant M146L. Aβ$_{42}$/Aβ$_{40}$ ratios and total Aβ levels (i.e., the sum of Aβ$_{40}$ and Aβ$_{42}$ values) were normalized to values obtained from DMSO-treated cells. Results shown were averages of two or three experiments performed in duplicate. CHO cell cultures treated with 40–60 µM sulindac sulfide showed a 50% reduction in Aβ$_{42}$/Aβ$_{40}$ ratios. No significant reduction in total Aβ level was observed. Therefore, treatment of CHO cells expressing APP and mutant PS-1 with the NSAID sulindac sulfide reduced the Aβ$_{42}$/Aβ$_{40}$ ratio by selectively reducing Aβ$_{42}$ secretion in a dose-dependent manner. This was confirmed in CHO cells that expressed wild type APP751 as well as those that expressed mutant APP V717F (data not shown). To rule out potential cell type-specific effects, Aβ secretion in response to sulindac sulfide treatment was examined in the human neuroglioma cell line HS683 that expressed APP695. FIG. 2 is a graph comparing Aβ$_{42}$/Aβ$_{40}$ ratios in HS683 cells expressing APP695 that were treated with DMSO with those of cells treated with various concentrations of sulindac sulfide. A dose-dependent reduction of Aβ$_{42}$ secretion, similar to that exhibited by CHO cells, was observed. Sulindac sulfide also reduced Aβ$_{42}$ secretion in kidney HEK293 cells and primary mouse embryonic fibroblasts (data not shown). No cell toxicity was observed at sulindac sulfide concentrations up to 100 µM (data not shown).

Example 9

Figure 3:
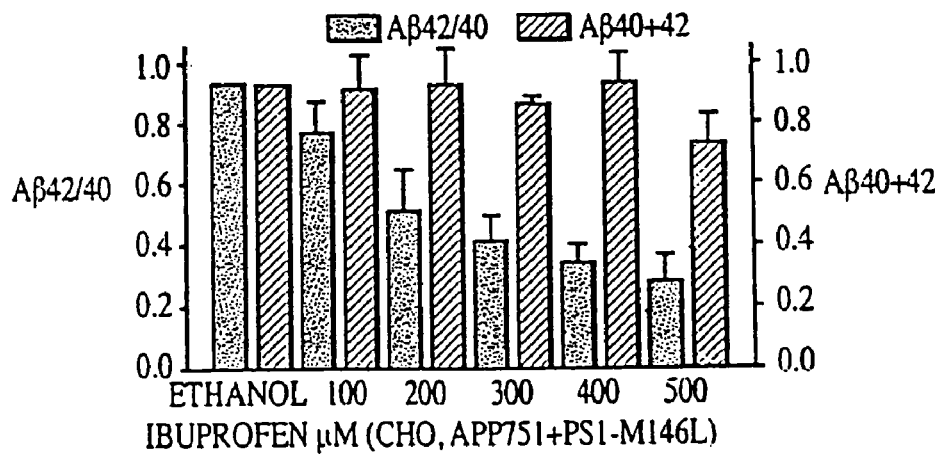
FIG. 3 is a bar graph summarizing $A\beta_{42}/A\beta_{40}$ ratios and total $A\beta$ levels determined for CHO cells expressing APP751 and PS-1 mutant M146L that had been treated with ethanol or with various concentrations of ibuprofen.
Figure 4:
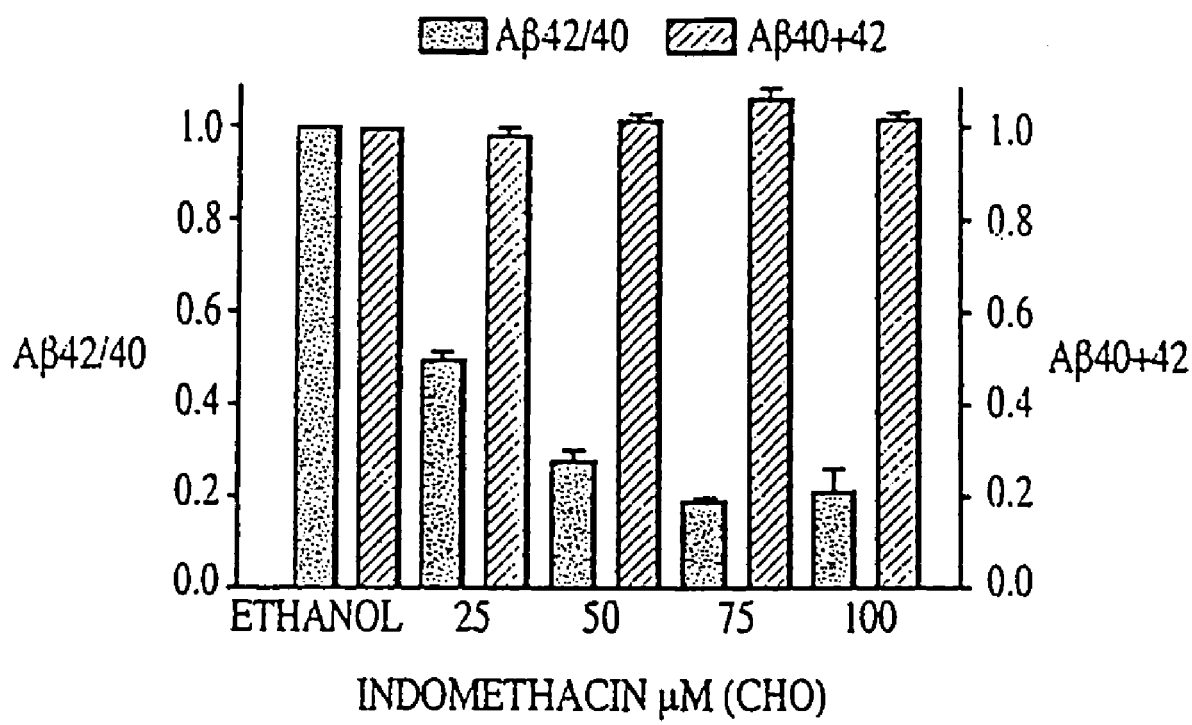
FIG. 4 is a bar graph summarizing $A\beta_{42}/A\beta_{40}$ ratios and total $A\beta$ levels determined for CHO cells expressing APP751 and PS-1 mutant M146L that had been treated with DMSO or with various concentrations of indomethacin.

Cells Treated with Other Non-selective COX-inhibitors such as Ibuprofen and Indomethacin Showed Reductions in Levels of Aβ$_{42}$ Secretion Cell cultures were treated with increasing concentrations of the NSAIDs ibuprofen and indomethacin. Aβ$_{40}$ and Aβ$_{42}$ levels in culture supernatants were analyzed using ELISA as described in Example 3. FIGS. 3 and 4 are graphs comparing Aβ$_{42}$/Aβ$_{40}$ ratios observed for CHO cells expressing APP751 and the PS-1 mutant M146L when treated with various concentrations of ibuprofen and indomethacin, respectively. Aβ$_{42}$/Aβ$_{40}$ ratios and total Aβ levels were normalized to values obtained from ethanol-treated cells. Results shown were averages of two or three experiments, each performed in duplicate. Dose dependent reductions in Aβ$_{42}$/Aβ$_{40}$ ratios by selective reductions of Aβ$_{42}$ secretion were observed for both ibuprofen and indomethacin. A 50% reduction in the Aβ$_{42}$/Aβ$_{40}$ ratio was reached at ibuprofen concentrations between 200–300 µM and at indomethacin concentrations between 25–50 µM. Total Aβ levels were not significantly affected at ibuprofen concentrations up to 500 µM (see FIG. 3) and at indomethacin concentrations up to 100 µM (see FIG. 4). No cell toxicity was observed in CHO cells treated with ibuprofen concentrations up to 1 mM or indomethacin concentrations up to 200 µM (data not shown).

Example 10

Reduction of Aβ42 Secretion is not Associated with COX-inhibitory Activity or with all NSAIDs The effect of sulindac sulfone on Aβ42 secretion was examined. Sulindac sulfone is an oxidation product of the pro-drug sulindac. Like sulindac sulfide, sulindac sulfone inhibits proliferation and induces apoptosis in human cancer cell lines in vitro (see Piazza et al. (1995) *Cancer Res* 55:3110–6). In contrast to sulindac sulfide, sulindac sulfone is devoid of any inhibitory effect on COX. Cell cultures were treated with increasing concentrations of sulindac sulfone. $A\beta_{40}$ and $A\beta_{42}$ levels in culture supernatants were analyzed using ELISA. When CHO cells expressing APP 751 were treated with sulindac sulfone, no changes in $A\beta_{42}/A\beta_{40}$ ratios were observed with sulindac sulfone concentrations of up to 400 µM (data not shown). The inability to reduce $A\beta_{42}$ secretion by the non-COX-inhibitor sulindac sulfone suggested an important mechanistic role for COX inhibition in the selective inhibition of $A\beta_{42}$ secretion by NSAIDs.

Figure 5:
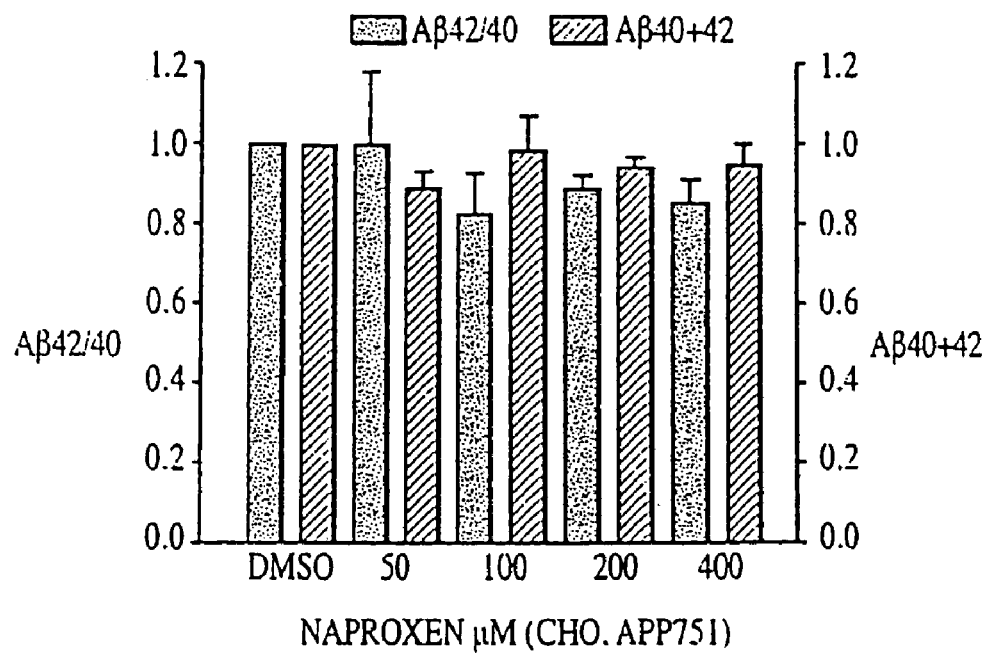
FIG. 5 is a bar graph summarizing $A\beta_{42}/A\beta_{40}$ ratios and total $A\beta$ levels determined for CHO cells expressing APP751 that had been treated with DMSO or with various concentrations of naproxen.
Figure 6:
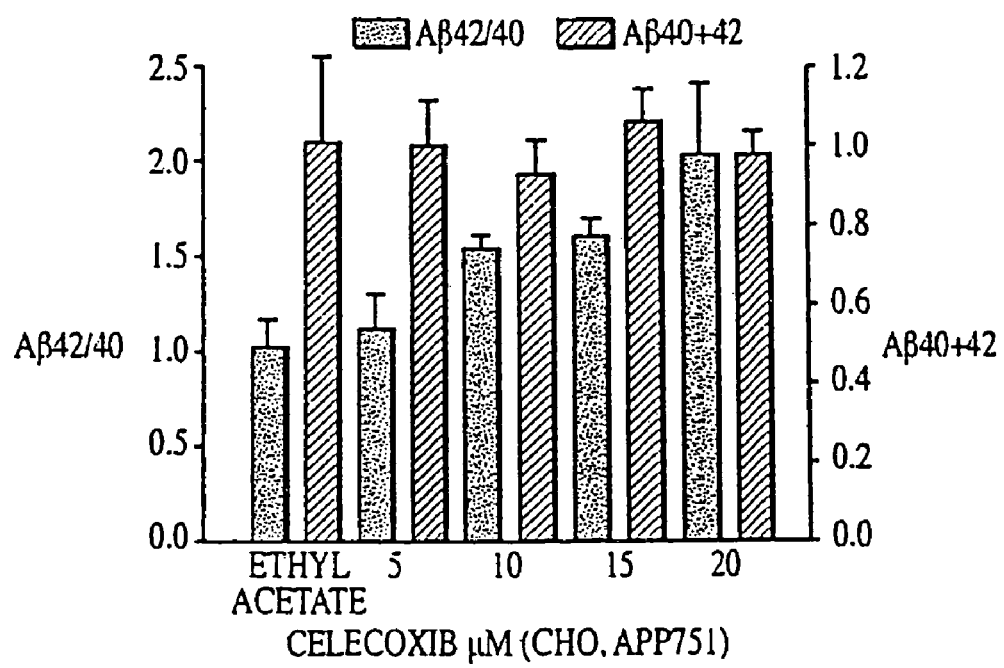
FIG. 6 is a bar graph comparing $A\beta_{42}/A\beta_{40}$ ratios and total $A\beta$ levels in CHO cells expressing APP751 that had been treated with ethyl acetate or various concentrations of celecoxib.

To determine whether reduction of $A\beta_{42}$ secretion is a common effect of all NSAIDs, other clinically useful NSAIDs were examined. Naproxen is a non-selective COX-inhibitor with an inhibition profile similar to sulindac and a structure similar to ibuprofen (see Cryer et al. (1998) *Am J Med* 104:413–21). Cell cultures were treated with increasing concentrations of naproxen and aspirin. $A\beta_{40}$ and $A\beta_{42}$ levels in cell culture supernatants were analyzed using ELISA. $A\beta_{42}/A\beta_{40}$ ratios and total Aβ levels were normalized to values obtained from DMSO-treated cultures. Averages of two or three experiments performed in duplicate are summarized in FIG. 5. Treatment of CHO cells expressing APP751 with naproxen, at concentrations up to 400 µM, did not change $A\beta_{42}/A\beta_{40}$ ratios and did not affect total Aβ levels (see FIG. 5). Similarly, no reductions in $A\beta_{42}$ secretion were observed when cultures were treated with aspirin concentrations of up to 3 mM (data not shown). Two selective inhibitors of COX-2, celecoxib and rofecoxib, also were examined to determine if they reduced $A\beta_{42}$ secretion. Celecoxib and rofecoxib were prepared from capsules using solvent extraction and recrystallization. NSAIDs were verified using NMR and mass spectrometry. CHO cells expressing APP751 were treated with various concentrations of celecoxib. FIG. 6 is a bar graph comparing $A\beta_{42}/A\beta_{40}$ ratios and total Aβ levels in cells treated with ethyl acetate or various concentrations of celecoxib. Results showed that 20CM celecoxib treatment induced a two-fold increase in $A\beta_{42}/A\beta_{40}$ ratio. The increase in $A\beta_{42}/A\beta_{40}$ ratio also was observed when human neuroglioma cells were tested (data not shown). The increase in $A\beta_{42}/A\beta_{40}$ ratio was not seen in cells treated with rofecoxib at 20 µM (data not shown). Diclofenac and NS-398, two other NSAIDs having preferential activities against COX-2, did not affect $A\beta_{42}/A\beta_{40}$ ratios or total Aβ levels. Table 1 summarizes selective and non-selective COX-inhibitors that were tested and results of these tests. Reduction of $A\beta_{42}$ secretion was not associated with all NSAIDs. (Note: peak NSAID concentrations used in these experiments were higher than what was required for complete inhibition of COX-1 and COX-2 activities in in vitro cell-based assays.)

TABLE 1

Non-selective and selective COX-inhibitors tested for effect on Aβ42 levels

| Drug | Highest conc. tested | Plasma | Aβ42/Aβ40 ratio | COX-1/COX-2 selectivity# (1 = equal activity) |
|---|---|---|---|---|
| Non-selective COX-inhibitors | | | | |
| Sulindac sulfide | 100 (µM) | 14.6 (µM) | selective decrease in Aβ42 | 0.61 |
| Indomethacin | 150 | 1.4 | selective decrease in Aβ42 | 22–58 |
| Ibuprofen | 750 | 40–111 | selective decrease in Aβ42 | 1.69 |
| Naproxen | 400 | 1.3 | no effect | 1.79 |
| Aspirin | 3000 | 111 | no effect | 166 |
| Meloxicam | 100 | 15 | no effect | .01–0.3 |
| Diclofenac* | 600 | 6.1 | no effect | .69 |
| Selective COX-2 inhibitors | | | | |
| NS-398* | 20 | | no effect | .07 |
| Celecoxib | 20 (µM) | 15 (nM) | selective increase in Aβ42 | .003 |
| Rofecoxib* | 20 (µM) | 3 (nM) | no effect | .001 |

Figure 7:
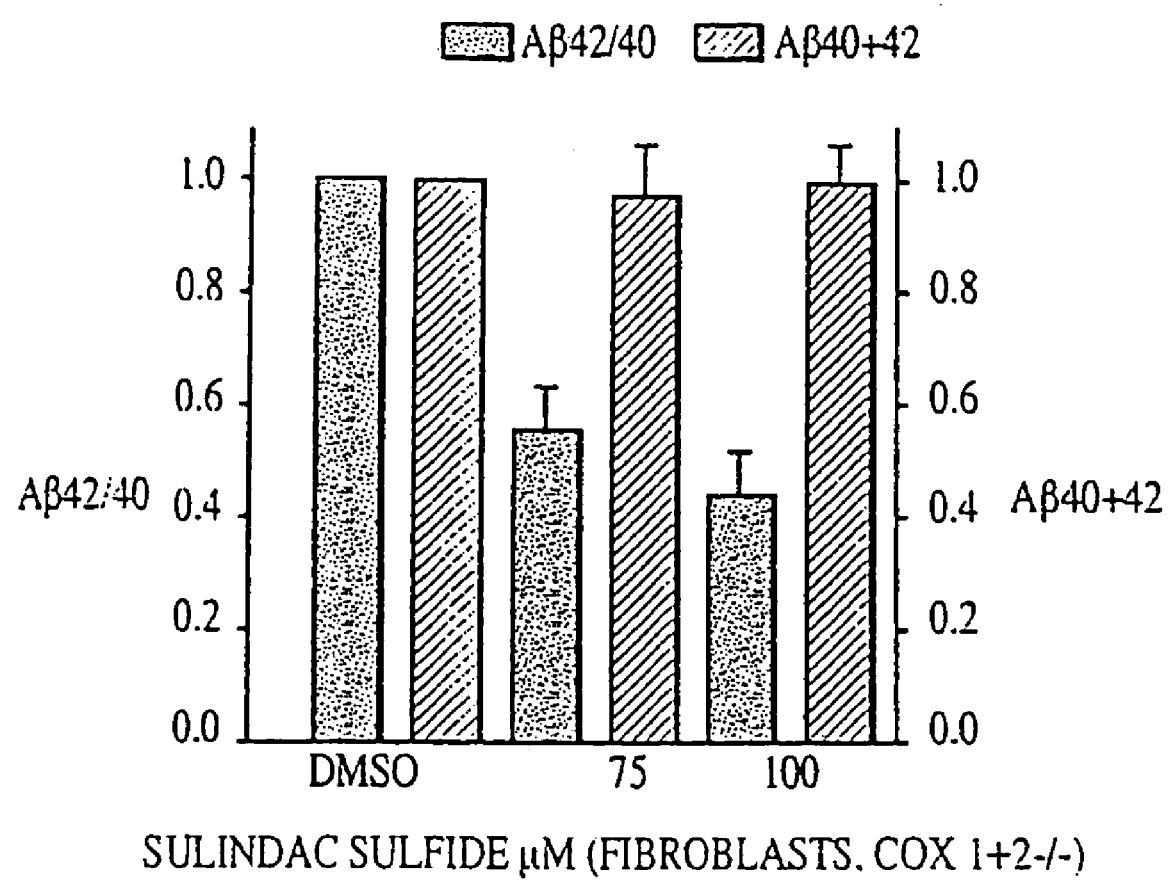
FIG. 7 is a bar graph summarizing $A\beta_{42}/A\beta_{40}$ ratios and total $A\beta$ levels determined for primary fibroblasts (from COX-1/COX-2 double-knockout mice) expressing APP 695 that had been treated with DMSO or various concentrations of sulindac sulfide.

To confirm that NSAID did not reduce $A\beta_{42}$ secretion through COX inhibition and though reduction of prostaglandin synthesis, cells devoid of COX-1 and COX-2 activities were treated with sulindac sulfide, and $A\beta_{42}/A\beta_{40}$ ratios were examined. Primary fibroblasts derived from COX-1/COX-2 double-knockout mice, described by Zhang et al. (1999) *J Exp Med* 190:451–59, were infected with an adenovirus vector that encoded APP695 (see Yuan et al. (1999) *J Neurosci Methods* 88: 45–54). Fibroblasts infected with the adenovirus vector expressing APP695 were treated with increasing concentrations of sulindac sulfide. Levels of Aβ forms in fibroblast culture supernatants were quantified using ELISA and results are summarized in FIG. 7. ($A\beta_{42}/A\beta_{40}$ ratios and total Aβ levels were normalized to values obtained from DMSO-treated cells. Results were the averages of two or three experiments, each performed in duplicate.) Sulindac sulfide reduced $A\beta_{42}$ secretion as well as the $A\beta_{42}/A\beta_{40}$ ratio of fibroblasts in a fashion similar to that seen with CHO and HS683 neuroglioma cells. Therefore, selective reduction of $A\beta_{42}$ was not mediated by COX inhibition.

Example 11

APP Processing by I and θ-Secretases, APP Turnover, and Notch Intramembrane Cleavage are not Affected by Sulindac Sulfide NSAIDs are the only compounds reported so far that change $A\beta_{42}/A\beta_{40}$ ratios by selectively decreasing $A\beta_{42}$ secretion. To determine if APP processing and notch intramembrane cleavage were affected in cells treated with NSAIDs, the following experiments were performed.

CHO cell cultures expressing APP751 were treated with increasing concentrations of sulindac sulfide. Cell lysates were prepared, and steady-state APP levels were examined using 4–12% gradient-gel electrophoresis and western blotting using the polyclonal antibody CT15. When western blot analysis was performed, neither a change in APP levels, nor an increase in CTF levels was observed in response to 60 TM or 80 TM sulindac sulfide treatment compared with levels observed for cells treated with DMSO. Unlike published γ-secretase inhibitors, sulindac sulfide did not induce detectable accumulation of APP CTFs. Therefore, β-secretase cleavage was not significantly affected by sulindac sulfide.

When western blot analysis was performed to detect soluble APP (sAPP) in culture supernatants using 5A3/IG7 monoclonal antibodies, results showed that there was no significant change in secretion of the APP ectodomain, (i.e., sAPP), in response to increasing concentrations of sulindac sulfide. Therefore, α-secretase cleavage was not significantly affected by sulindac sulfide.

APP turnover in the presence of sulindac sulfide was examined by (1) pulse labeling CHO cells with $^{35}$S-methionine and (2) determination of APP half-life. All values were normalized to a signal obtained at the end of pulse labeling. When the APP half-life in cells treated with DMSO was compared with APP half-life in cells treated with sulindac sulfide at 25 or 125 μM, APP half-life after treatment with 25 or 125 μM sulindac sulfide was similar to APP half-life after treatment with DMSO. Therefore, APP turnover was not altered significantly in the presence of sulindac sulfide.

A significant fraction of Aβ is produced and released in the endocytic pathway after internalization of APP from the cell surface (see Koo et al. (1994) *J Biol Chem* 269: 17386–9). The effect of sulindac sulfide on this endocytic pathway was examined with an APP internalization assay described by Koo et al. (1996) *J Cell Sci* 109:991–8. APP internalization was expressed as a ratio of cell surface APP versus internalized APP. When APP internalization in cultures treated with DMSO was compared with APP internalization in cultures treated with sulindac sulfide at 60 or 80 μM, the ratio of cell surface APP to internalized APP was not altered in cells treated with sulindac sulfide compared to cells treated with DMSO alone. Therefore, it was concluded that APP internalization was unchanged after sulindac sulfide treatment.

Notch intramembrane cleavage and formation of NICD were analyzed in kidney HEK293 cells. The myc-tagged NotchΔEMV construct encoding a constitutively cleaved Notch variant was transiently transfected into HEK293 cells. Cell cultures were treated with 125 μM sulindac sulfide for 36 hours. Then they were pulse labeled with $^{35}$S-methionine for thirty minutes and chased for two hours. Cell lysates were prepared and subjected to immunoprecipitation with monoclonal antibody 9E10. Immunoprecipitated proteins were subjected to SDS-PAGE and phosphor imaging analyses. When amounts of NICD immunoprecipitated from lysates of cells treated with DMSO were compared with amounts immunoprecipitated from lysates of cells treated with sulindac sulfide, results showed that treatment with sulindac sulfide did not impair Notch cleavage and NICD formation. (Cells transfected with a construct encoding only the NICD domain were used for identification of the cleavage fragment.) Similarly, treatment with 500 μM ibuprofen or 150 μM indomethacin did not cause accumulation of APP-CTFs or inhibition of Notch cleavage (data not shown). Overall, these results demonstrated that NSAID treatment did not significantly perturb APP processing or γ-secretase activity. This, however, did not rule out modulation of γ-secretase activity as a mechanism of action for NSAIDs. The selective reduction in $A\beta_{42}$ secretion could be reflected only in minor changes of γ-secretase activity that may not be detectable in the assays described above.

Example 12

Figure 8A:
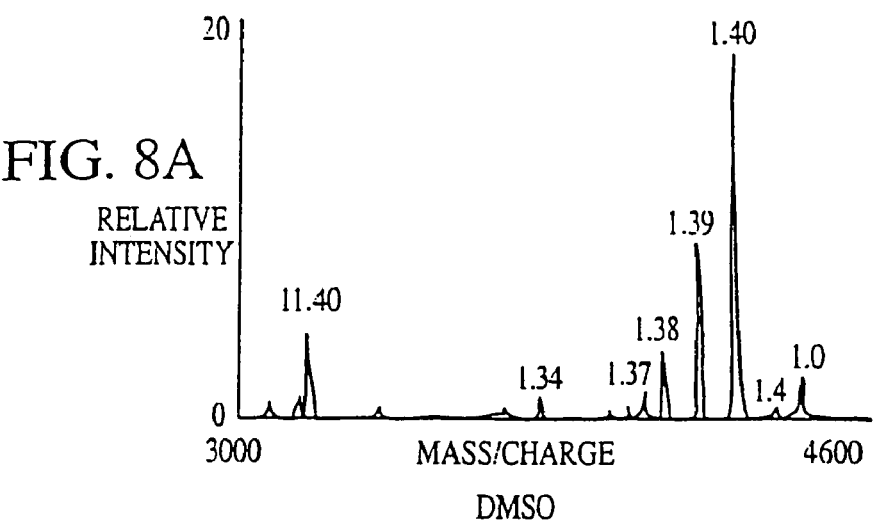
FIG. 8 is two representative mass spectra of $A\beta$ species secreted by CHO cells expressing APP751 after treatment with DMSO or 100 µM sulindac sulfide.
Figure 8B:
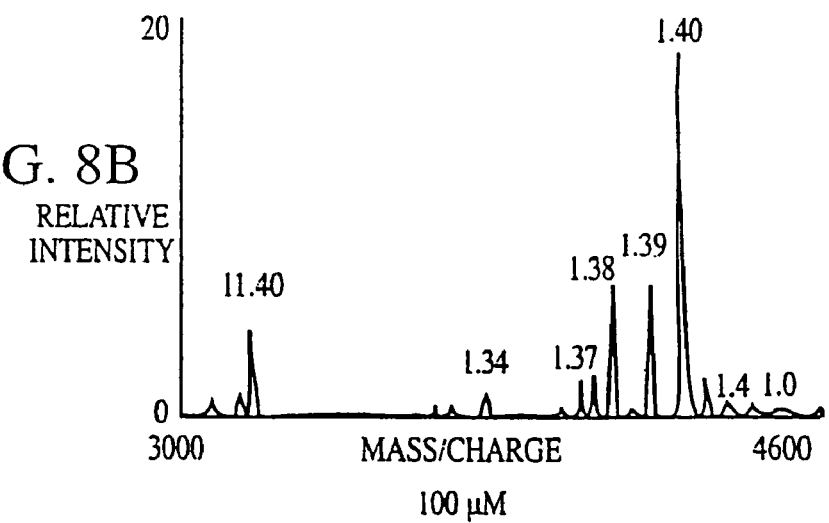
Figure 9:
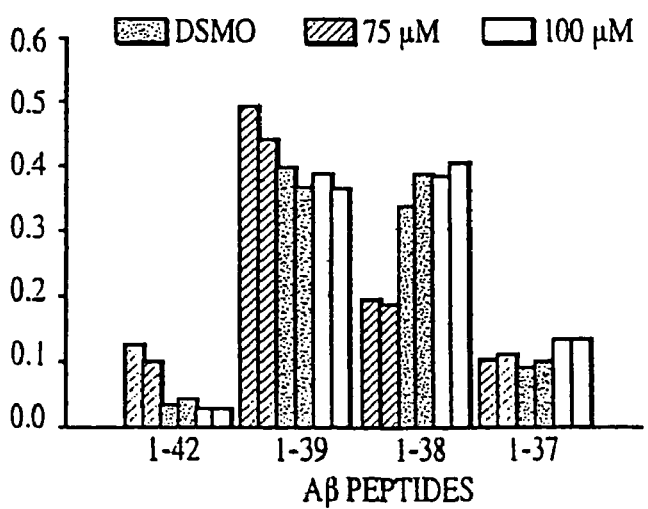
FIG. 9 is a bar graph illustrating ratios of $A\beta_{1-42}$, $A\beta_{1-39}$, $A\beta_{1-38}$, and $A\beta_{1-37}$ to $A\beta_{1-40}$ in cells treated with DMSO or sulindac sulfide.

Reduction in $A\beta_{42}$ Secretion was Accompanied by a Dose-dependent Increase in $A\beta_{1-38}$ Species To examine Aβ species secreted by cells treated with sulindac sulfide, immunoprecipitation and mass spectrometry analyses were performed. FIG. 8 is two representative mass spectra of Aβ species secreted by CHO cells expressing APP751 after treatment with DMSO or after treatment with 100 μM sulindac sulfide. After treatment with 75–100 μM sulindac sulfide, a strong reduction in $A\beta_{42}$ secretion was observed. Levels of $A\beta_{40}$, however, were largely unaffected. Various Aβ species including $A\beta_{1-42}$, $A\beta_{1-39}$, $A\beta_{1-38}$, and $A\beta_{1-37}$ were quantified. FIG. 9 is a bar graph comparing ratios of each of these species to $A\beta_{40}$, i.e. $A\beta_{1-x}/A\beta_{1-40}$ ratios, at 75 or 100 μM sulindac sulfide. Duplicate measurements were used in generating the bar graph. Reductions in $A\beta_{42}/A\beta_{40}$ ratios were accompanied by two-fold increases in $A\beta_{1-38}/A\beta_{1-40}$ ratios. Increases in $A\beta_{1-38}$ levels were dose-dependent. Other Aβ peptide levels did not vary consistently between cells treated with DMSO or with sulindac sulfide.

Mass spectrometry results demonstrating reductions in $A\beta_{42}$ secretion with concomitant increases in $A\beta_{1-38}$ secretion were confirmed by immunoprecipitation. Aβ polypeptides were immunoprecipitated from culture supernatants of CHO cells expressing APP751 and mutant PS-1. Immunoprecipitates were separated on an SDS-urea gel system that can resolve individual Aβ species (see Wiltfang et al. (1997) *Electrophoresis* 18:527–32). Standard $A\beta_{1-38}$, $A\beta_{1-40}$, and $A\beta_{1-42}$ peptides were included for identification of different Aβ species. When changes in $A\beta_{38}$, $A\beta_{40}$, and $A\beta_{42}$ levels in CHO cells treated with DMSO were compared with those in cells treated with 60 μM or 80 μM of sulindac sulfide, a reduction in the intensity of an immuno-reactive band corresponding to $A\beta_{42}$ was observed. This reduction was matched by an equivalent increase in the intensity of an immuno-reactive band corresponding to $A\beta_{1-38}$.

Two potential mechanisms may explain this unprecedented change in Aβ production after NSAID treatment. Sulindac sulfide could reduce $A\beta_{42}$ secretion by shifting γ-secretase activity towards production of $A\beta_{1-38}$. Alterna tively, it may stimulate a novel proteolytic activity that converts $A\beta_{42}$ into shorter $A\beta$ species such as $A\beta_{1-38}$.

Koo et al. (1994) *J Biol Chem* 269:17386–9 and others reported that APP processing in the endocytic pathway leads to the generation and release of both $A\beta_{40}$ and $A\beta_{42}$ into culture supernatant. To examine the intracellular pool of $A\beta_{42}$ in APP mutants that lack the endocytic signal, CHO cells expressing an internalization-deficient APP polypeptide lacking 43 amino acids in the cytoplasmic tail were used (Perez et al. (1999) *J Biol Chem* 274:18851–6). Levels of cellular and secreted $A\beta_{42}$ and $A\beta_{40}$ in cells expressing wild type APP and in cells expressing mutant APP were compared using ELISA. Results indicated that in the absence of the cytoplasmic tail, levels of $A\beta_{40}$ and $A\beta_{42}$ secreted by cells expressing mutant APP were diminished compared to cells expressing wild type APP. In addition, in the absence of a cytoplasmic tail, cellular $A\beta_{40}$ levels were reduced while cellular $A\beta_{42}$ levels were not reduced.

Example 13

NSAID Treatment of Tg2576 Transgenic Mice

NSAIDs were dissolved in an appropriate vehicle. Dimethyl sulfoxide (DMSO), ethanol, and ethyl acetate are some examples. The NSAID solution was mixed with Kool-Aid and administered orally using a medicine dropper. For three days, equal doses were administered every four hours, totaling 50 mg/kg/day. At two hours after the final doses were administered, animals were sacrificed, and SDS soluble $A\beta_{40}$ and $A\beta_{42}$ were analyzed using ELISA.

Example 14

Treatment of Animals with Ibuprofen Reduces $A\beta_{42}$ Levels

Figure 10:
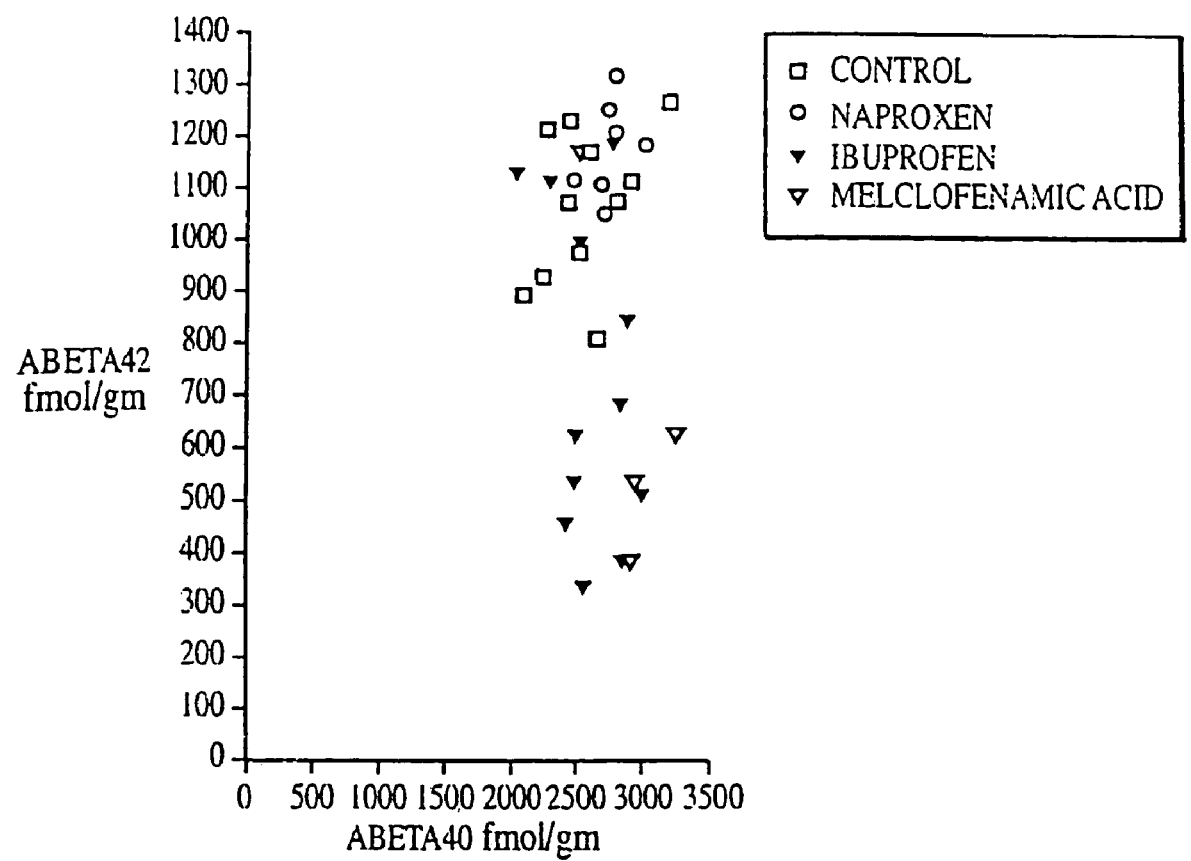
FIG. 10 is a scattergram of $A\beta_{40}$ and $A\beta_{42}$ levels in the brains of Tg2576 mice after short-term NSAID treatment.

To determine whether acute ibuprofen treatment of mice would reduce $A\beta_{42}$ levels, three month-old Tg2576 mice expressing APP695 containing the 'Swedish" mutation (APP695NL) were used. Three month old mice have high levels of soluble $A\beta$ in the brain but no $A\beta$ deposition (see Hsiao et al. (1996) *Science* 274:99–102). Mice were given naproxen, ibuprofen, or meclofenamic acid as described in Example 13. Mice treated with ibuprofen (n=12) were compared with those untreated (n=11), treated with naproxen (n=7), or treated with meclofenamic acid (n=4). Brain levels of SDS-soluble $A\beta_{40}$ and $A\beta_{42}$ were measured using ELISA. Table 2 summarizes $A\beta_{40}$ and $A\beta_{42}$ levels determined for the control group and the naproxen, ibuprofen, and meclofenamic acid-treated groups. Treatment with ibuprofen or meclofenamic acid for three days resulted in approximately 30% reduction in $A\beta_{42}$ levels in the brain, while no change was observed in $A\beta_{40}$ levels (see FIG. 10). No reduction in $A\beta_{42}$ levels was observed for naproxen-treated mice. These data were consistent with the rapid onset of $A\beta_{42}$ reduction in cell culture studies and illustrated that cell culture experiments were able to predict in vivo efficacy. In addition, these data suggested that ibuprofen treatment could prevent amyloid pathology by decreasing $A\beta_{42}/A\beta_{40}$ ratio in the brain.

TABLE 2

Brain levels of Aβ after acute dosing of Tg2576 mice (mean ± SD)

|  | Control (n = 11) | Naproxen (n = 7) | Ibuprofen (n = 12) | Meclofenamic acid (n = 4) |
|---|---|---|---|---|
| Aβ40 (fmol/gm) | 2603 ± 314 | 2786 ± 179 | 2620 ± 246 | 2932 ± 289 |
| Aβ42 | 1074 ± 145 | 1182 ± 93 | 734 ± 302* | 679 ± 343** |
| % Aβ42 | 29.3 ± 2.9 | 29.8 ± 1.6 | 21.5 ± 7.7* | 18.6 ± 8.7** |

*= $p < 0.05$; **= $p < 0.01$, Dunnett's test

Example 15

NSAIDs, NSAID Derivatives, and NSAID Analogues

Figures 2, 11:
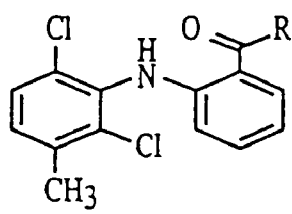
FIG. 11 is a summary of the structures of indomethacin and meclofenamic acid, possible side chain modifications, and the effects of these modifications on COX-1 and COX-2 activities.

NSAIDs that are screened for the ability to reduce $A\beta_{42}$ levels include: FDA-approved NSAIDs, NSAIDs derivatives, and NSAID analogues most potent for reducing $A\beta_{42}$ levels, newly synthesized derivatives and analogues of the most potent NSAIDs, and NSAIDS known to target pathways other than COX pathways. FDA-approved NSAIDs include ibuprofen, naproxen, dicolfenac, aspirin, indomethacin, fenoprofen, flurbiprofen, ketorolac. Derivatives of the most potent NSAIDs include aryl propionic acid derivatives such as ibuprofen and fenoprofen, and the anthranilic acid derivatives (also called amino carboxylic acid derivatives) such as the meclofenamic acid series and flufenamic acid. (NSAIDs in both series share a similar core structure of either a diphenyl ketone or dephenyl ether.) Other derivatives or analogues that are screened for the ability to reduce $A\beta_{42}$ levels include flufenamic acid, indomethacin, and meclofenamic acid derivatives and analogues (see FIG. 11 and Kalgutkar et al. (2000) *J of Med Chem* 43:2860–70). Newly synthesized NSAID derivatives or analogues include novel biphenyl amines (FIG. 12) and diphenyl ketones. Examples of NSAIDs that target additional pathways to COX include LOX inhibitors.

Once a set of NSAIDs, NSAID derivatives, or NSAID analogues having potent ability to reduce $A\beta_{42}$ levels is obtained, a pharnacophore search is performed to identify other NSAIDs structurally similar to those in the set. If a large number of candidates are identified, the structurally similar NSAIDs are subjected to a secondary structural screen using a computer-based molecular docking algorithm known as EUDOC. In the second structural screen, crystal structures and COX-1/COX-2 binding pockets are used to identify a subset consisting of NSAIDs structurally similar to those that have potent ability to reduce $A\beta_{42}$ levels but do not bind COX-1 or COX-2. NSAIDs predicted to bind to COX and those predicted to not bind to COX are used as controls.

NSAIDs, NAID derivatives, and NSAID analogues can be obtained commercially or they can be chemically synthesized. Novel NSAIDs, NSAID derivatives, or NSAID analogues with unknown effects on COX activity are tested using in vitro COX-1 and COX-2 assays to determine if there is an affect on COX activity. Commercially available kits from Oxford biochemicals are used for COX inhibition assays.

Example 16

Figure 13:
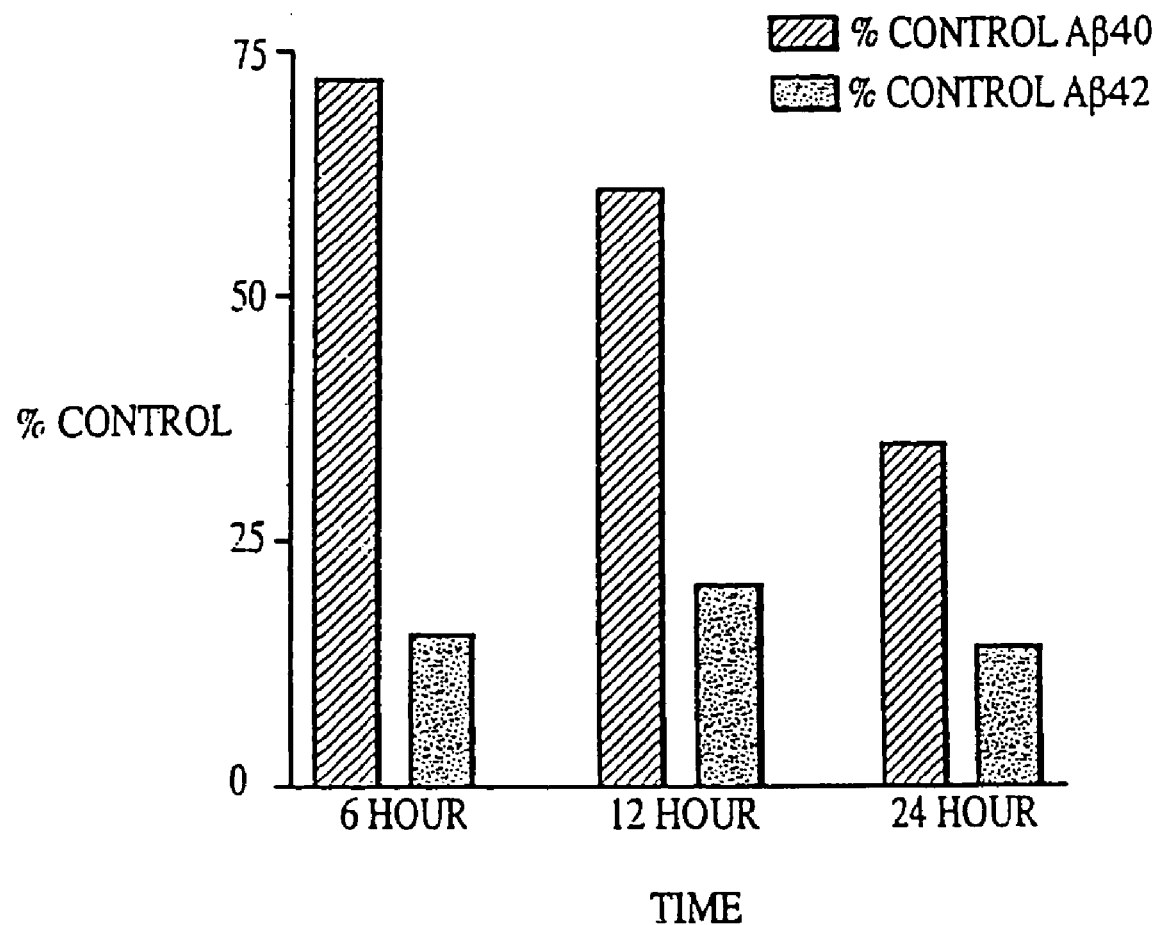
FIG. 13 is a time course of $A\beta_{42}$ reduction in CHO APP695NL,I,his cell cultures treated with meclofenamic acid.

Determination of Optimal Screening Interval for Detecting Selective Reduction of β42 Levels To determine the optimal treatment interval for examining selective reduction of $A\beta_{42}$ levels, CHO-APP695NL,I,his cell cultures were treated with the vehicle, or treated with ibuprofen or meclofenamic acid for six, twelve, or twenty-four hours. $A\beta_{40}$ and $A\beta_{42}$ levels in culture supernatants were determined for each time points using ELISA. FIG. 13 is a bar graph demonstrating that selective reduction of $A\beta_{42}$ was detectable at six hours when cells were treated with meclofenamic acid. Similar results were observed for ibuprofen (data not shown).

Example 17

Primary in vitro Screening

In a primary screen, the effects of NSAIDs on $A\beta_{42}$ secretion by a CHO cell line that expressed APP (CHO-APP695NL,I,his) were examined. Duplicate cell cultures were treated with (a) a vehicle, (b) 10 µM of NSAID, or (c) 100 µM of NSAID.

To determine $A\beta_{40}$ and $A\beta_{42}$ levels, six-hour culture supernatants taken from cells grown in a single well of a twenty-four-well plate were used in end-specific $A\beta_{40}$ and $A\beta_{42}$ ELISAs (Suzuki, et al. (1994) *Sci* 264:336–1340). $A\beta_{40}$ and $A\beta_{42}$ levels of cultures treated with NSAID were compared with those of cultures treated with the vehicle alone. Concentrations of 100 µM Ibuprofen and 10 µM meclofenamic acid were used as positive controls. Results, in Table 3, indicated that some NSAIDs selectively reduce $A\beta_{42}$ levels, but at the concentrations tested, many do not. NSAIDs were classified based on a 20% change in Aβ levels observed in NSAID-treated versus vehicle treated cells. Classification was made based on a 20% change because the data showed a 10% accuracy variance. When classification was made based on a 20% change, all NSAIDs screened, with the exception of two, were classified in the same category with repeated testing. Two NSAIDs, shown in bold italic, gave results that altered their categorization upon re-screening; classification was resolved after a third test. These results confirmed the data described in Examples 8–10, as the NSAIDs that were shown to selectively lower $A\beta_{42}$ initially also reduced $A\beta_{42}$ in this screen. Of the newly synthesized biphenyl amines, meclofenamic, mefenamic, and flufenamic acid selectively reduced $A\beta_{42}$ levels, while tolfenamic acid did not. NSAIDs that caused either selective reduction of $A\beta_{42}$ levels or reduction in both $A\beta_{40}$ and $A\beta_{42}$ levels are subjected to a secondary screen.

TABLE 3

Effects of NSAIDs on secreted Aβ.

| Compound | Type | % Control Aβ40 | % Control Aβ42 | % Control % Aβ42 |
|---|---|---|---|---|
| ↓Aβ42 no effect on Aβ40 | | | | |
| Sulindac Sulfide 10 TM | Cox-1, 2 | 97% | 57% | 65% |
| Flufenamic Acid 10 TM | Cox-1, 2 | 99% | 64% | 70% |

TABLE 3-continued

Effects of NSAIDs on secreted Aβ.

| Compound | Type | % Control Aβ40 | % Control Aβ42 | % Control % Aβ42 |
|---|---|---|---|---|
| Ibuprofen 100 TM | Cox-1, 2 | 95% | 74% | 81% |
| Ibuprofen 10 TM | Cox-1, 2 | 102% | 80% | 82% |
| Flurbiprofen 100 TM | Cox-1, 2 | 93% | 70% | 80% |
| Fenoprofen 100 TM | Cox-1, 2 | 102% | 60% | 63% |
| Mefenamic Acid 100 TM | Cox-1, 2 | 116% | 78% | 72% |
| Indomethacin 100 TM | Cox-1, 2 | 101% | 69% | 68% |
| ↓Aβ42 > ↓Aβ40 | | | | |
| NPPB 10 Tm | Cox-1, 2 | 81% | 48% | 66% |
| Carprofen 100 TM | Cox-1, 2 | 58% | 48% | 86% |
| Meclofenamic Acid 10 TM | Cox-1, 2 | 39% | 13% | 37% |
| ↓Aβ40 no effect on Aβ42 | | | | |
| APHS 10 TM | Cox2 > Cox1 | 50% | 114% | 178% |
| Resveratrol 10 Tm | Cox-1 | 75% | 107% | 130% |
| ↓Aβ40 and ↑Aβ42 | | | | |
| Meloxicam 10 TM | Cox-1, 2 | 64% | 122% | 158% |
| SC560 10 TM | Cox-1 > Cox-2 | 47% | 166% | 227% |
| Guaiazulene 100 TM | Cox-1, 2 | 70% | 124% | 156% |
| ↑Aβ42 | | | | |
| NS398; 10 Tm | Cox-2 > Cox-1 | 101% | 146% | 132% |
| Ketorlolac 10 TM | Cox-1, 2 | 84% | 131% | 142% |
| Benzydamine 100 TM | Cox-1, 2 | 90% | 128% | 132% |
| ↑Aβ40 and/or ↑Aβ42 | | | | |
| Suprofen 100 TM | Cox-1, 2 | 126% | 129% | 102% |
| Indoprofen 100 TM | Cox-1, 2 | 116% | 126% | 107% |
| Nabumetone 100 TM | Cox-1, 2 | 157% | 103% | 70% |
| Piroxicam 100 TM | Cox-1, 2 | 142% | 101% | 75% |
| No Effect on Aβ | | | | |
| Acetylsalicylic acid 100 TM | Cox-1 > Cox-2 | 93% | 99% | 104% |
| Ketoprofen 100 TM | Cox-1, 2 | 88% | 107% | 117% |
| Fenbufen 100 TM | Cox-1, 2 | 100% | 109% | 107% |
| Naproxen 100 TM | Cox-1, 2 | 107% | 112% | 104% |
| Isoixicam 100 uM | Cox-1, 2 | 109% | 112% | 103% |
| Tenoxicam 100 TM | Cox-1, 2 | 80% | 92% | 112% |
| Tolfenamic Acid 100 TM | Cox-1, 2 | 84% | 95% | 110% |
| Diclofenac; 100 Tm | Cox-1, 2 | 88% | 87% | 100% |
| Etodolac 100 TM | Cox-1, 2 | 85% | 109% | 120% |
| Acemetacin 100 TM | Cox-1, 2 | 110% | 101% | 93% |
| Niflumic Acid | Cox-1, 2 | 120% | 107% | 85% |
| Dapsone | Anti-Bacterial | 99% | 80% | 84% |
| Sulindac Sulfone | No-Cox | 109% | 97% | 92% |
| Nimesulide | Cox-1, 2 | 105% | 116% | 116% |
| Suxibuzone | Cox-1, 2 | 82% | 107% | 129% |
| Diflunisal | Cox-1, 2 | 90% | 103% | 112% |

Example 18

Secondary and Tertiary in vitro NSAID Screening

In a secondary screen, an extended dose-response study in which CHO cell cultures are treated with 1 nM to 1 mM of NSAID is performed. Dose response studies are used to estimate $IC_{50}$ values for maximum reduction of Aβ levels as well as to identify NSAIDs that have toxic effects. A secondary screen is performed for all FDA-approved NSAIDs that reduce $A\beta_{42}$ levels in cell cultures.

In a tertiary screen, Aβ production, sAPP production, and toxicity in a human H4 neuroglioma cell line that expressed APP are examined for all FDA-approved NSAIDs and novel NSAIDs that selectively reduce $A\beta_{42}$ levels. Three doses of each NSAID are tested. The first is a dose that is expected to cause maximum reduction of $A\beta_{42}$ levels. The second dose is one that reduces $A\beta_{42}$ levels by 50% of the maximum value, while the third dose is one that reduces $A\beta_{42}$ levels by 10–20% of the maximum value. Tertiary screens are performed on the most potent NSAIDs identified by secondary screens.

NSAID toxicity is measured using an MTS assay (see Example 1) and a lactate dehydrogenase (LDH) release assay (Promega Corp, Madison, Wis.).

Example 19

Acute Single-dose Studies to Identify NSAIDs having in vivo Activity

To determine whether NSAIDs that selectively reduce SDS-soluble $A\beta_{42}$ levels in cell culture studies also reduce brain $A\beta_{42}$ levels, in vivo studies using Tg2576 mice are performed.

Mice of either sex are used for acute studies. Each experimental group, however, is performed using mice of the same sex. Power calculations, based on past measurements of variability of Tg2576 brain $A\beta$ levels, indicate that an "n" of five mice per study group gives an 80% chance of detecting a difference of 20% or more at $p<0.05$. These calculations are supported by experiments on wortmanin treated and $A\beta_{42}$ immunized Tg2576 mice, in which significant changes in $A\beta$ levels, even between groups of three to four mice, were noted (Haugabook et al. (2000) Faseb J). Although in most studies there are five mice per experimental group, in some instances, additional mice are used to account for loss due to death or illness. The use of additional mice also increases the power of ancillary studies such as those involving behavior, as sometimes, the number of mice needed to obtain a useful result is not known.

NSAIDs are prepared and administered to three-month-old Tg2576 mice as described in Example 13. To avoid extensive testing of NSAIDs that are not active in vivo, high doses of NSAIDs are used initially. NSAIDs are administered every four to eight hours; exact doses and dose schedules are determined from $LD_{50}$ values, half-lives, and in vitro dose response studies. In general, a maximum dose that is non-toxic, typically ranging from $\frac{1}{10}$ to $\frac{1}{5}$ of the $LD_{50}$ value of the NSAID, is used. If the $LD_{50}$ and other pharmacokinetic data of a given NSAID are unknown, their values are estimated using those of the nearest structural analogue.

To monitor toxicity, weights of a mouse before and after the study are compared. In addition, one mouse from each treatment group is subjected to a liver function test (LFT) in which blood levels of two liver enzymes, SGOT and SGPT, are determined. SGOT and SGPT are sensitive markers of liver toxicity. Furthermore, renal function, indicated by blood urea nitrogen (BUN) levels, is determined. Tests for liver and renal functions are performed by Anilitics (Gaithersburg, Md.), a company that specializes in these tests. Those NSAIDs having toxic effects at high doses are not used in long-term studies unless their effectiveness and lack of toxicity at lower doses are established.

Following a three-day administration schedule, mice are sacrificed; $A\beta$ levels in plasma, brain, and CSF are determined; levels of NSAIDs in plasma are determined; and mice are examined for signs of toxicity. NSAIDs that selectively reduce SDS-soluble $A\beta_{42}$ levels by more than 20–30% are examined in multiple dose response studies.

Example 20

Multiple-dose Studies to Identify Doses useful for in vivo Long-Term Animal and Human Studies NSAIDs that reduce $A\beta_{42}$ levels in vivo, at high doses, are administered to groups of three mice at high, medium, and low doses using the same dosing regimen described in Example 19. A high dose is the amount used in the single dose screen of Example 19, while medium and low doses are determined by inference from in vitro dose response studies described in Example 18. Those NSAIDs more potent than ibuprofen in vitro, (i.e., those that have $IC_{50}$ values required for maximum reduction of $A\beta_{42}$ levels that are less than a mid TM value) are examined over a wide range of doses. For example, doses representing $\frac{1}{50}$ to $\frac{1}{10}$ of the $IC_{50}$ value are used in the multiple dose analysis. NSAIDs having similar in vitro $IC_{50}$ values to ibuprofen are tested over a more limited range. For example, doses representing $\frac{1}{10}$ to $\frac{1}{3}$ of the $IC_{50}$ value are used in the multiple dose analysis. Analyses of $A\beta$ are performed as described for single dose studies. To identify plasma NSAID levels that correlate with $A\beta_{42}$ reduction in vivo, a plasma NSAID level is determined for each dose examined using the HPLC method described in reference 64 and adapted for each particular NSAID. Data pertaining to plasma NSAID levels in these multiple dose studies are used as reference values for both long-term animal studies where NSAIDs are administered in feed, as well as for subsequent human studies.

Example 21

Effects of NSAIDs on in vivo COX Activity

To determine if concentrations of NSAIDs used are sufficient to mediate anti-inflammatory effects, novel NSAIDs are examined for their in vivo COX inhibitory activities and anti-inflammatory activities. For this study, the carrageneenan-induced footpad edema assay, described in Kalgutkar et al. (2000) J of Med Chem 43:2860–70, is performed on mice prior to sacrifice. For NSAIDs that do not reduce $A\beta_{42}$ levels, the assays are performed on mice treated with NSAIDs at levels equivalent to that administered in long-term studies.

Example 22

NSAIDs used in Long-term Preventative and Therapeutic Studies

To determine whether the effects of NSAIDs on amyloid deposition in an animal model are attributable to direct inhibition of $A\beta_{42}$ accumulation, or reduction in inflammatory processes in the brain, or both, the following groups of NSAIDs are examined in long-term preventative and therapeutic tests. NSAIDs that selectively reduce $A\beta_{42}$ levels but lack anti-inflammatory properties, NSAIDs that selectively reduce $A\beta_{42}$ levels and have anti-inflammatory properties, or NSAIDs that have no effect on $A\beta_{42}$ levels but have anti-inflammatory properties are examined in both preventative and therapeutic studies. Ibuprofen is used to examine indirect inflammatory-mediated effects on $A\beta$ deposition and direct effects caused by reduction of $A\beta_{42}$ levels, since it reduces $A\beta_{42}$ levels and has anti-inflammatory properties. Celecoxib and naproxen, non-selective and selective Cox inhibitors, respectively, that do not cause reduction of $A\beta_{42}$ levels are used to examine $A\beta_{42}$-independent inflammatory-mediated effects. NSAIDs examined in both preventative and therapeutic studies include those that exhibit one of these three properties: selectivity for $A\beta_{42}$ reduction relative to COX inhibition, $A\beta_{42}$ reduction and COX-2 selectivity, or solely increased potency for $A\beta_{42}$ reduction in vivo.

Example 23

Long-term NSAID Dosing for Preventative and Therapeutic Trials

Long-term dosing of mice is achieved through feed. Feed containing the desired concentration of NSAID can be obtained from commercial entities. Prior to long-term preventative or therapeutic studies, successful administration of a chosen dose of NSAID through feed is verified using the following experiment. First, an NSAID concentration effective in reducing $A\beta_{42}$ levels in acute studies, when administered by dropper, is chosen. This concentration corresponds to the lowest dose that can generate a maximum reduction in $A\beta_{42}$ levels. In the case of an NSAID that does not reduce $A\beta_{42}$ levels, a concentration sufficient to cause anti-inflammatory effects is chosen. In the case of ibuprofen, the dose that reduces $A\beta_{42}$ levels also is a dose that causes anti-inflammatory effects. Feed containing the chosen concentration of NSAID is used in a short-term trial to compare mice given NSAID by dropper to mice given NSAID incorporated into feed. The reduction in $A\beta_{42}$ levels as well as peak plasma levels of NSAID are determined for mice given NSAID by dropper and mice given NSAID through feed. If levels of $A\beta_{42}$ reduction and peak plasma levels of NSAID in the two groups are comparable, then the chosen amount of NSAID is achieved through feeding, and long-term preventative or therapeutic studies are performed. If levels of $A\beta_{42}$ reduction and peak plasma levels of NSAID in the two groups are not comparable, then the concentrations of NSAID in feeds are altered appropriately until reduction in $A\beta_{42}$ levels and peak plasma levels of NSAID in the two groups of mice are comparable.

Example 24

Determination of Peak Plasma Levels of NSAIDs

Techniques for determination of ibuprofen, fenoprofen, and meclofenamic acid levels in plasma are described in Canaparo et al. (2000) *Biomedical Chromatography* 14:219–26; and Koup et al. (1990) *Biopharmaceutics & Drug Disposition* 11:1–15. In general, an internal standard is added to a plasma sample. The sample is acidified and subjected to organic solvent extraction. The organic phase is dried, dissolved in a small volume, and subjected to HPLC using a C18 column. Calibration and standardization are carried out using untreated plasma spiked with NSAID for construction of a calibration curve.

Example 25

CSF Collection

Mice are anesthetized with pentobarbital (30–50 mg/kg). An incision from the top of the skull to the mid-back is made and the musculature from the base of the skull to the first vertebrae is removed to expose the meninges overlying the cisterna magna. The animal is placed on a narrow platform in an inverted fashion beneath a dissecting microscope. The tissue above the cisterna magna is excised with care not to puncture the translucent meninges. The surrounding area is cleaned gently with the use of cotton swabs to remove any residual blood or other interstitial fluid. The dilated cisterna magna containing CSF is easily visible at this point. In addition to the cerebellum, brain stem, and spinal cord, an extensive vascular network also is visible. A micro needle and a polypropylene narrow bore pipette are aligned just above the meninges. With care not to disrupt any of the underlying vasculature, the micro needle is slowly inserted into the cistern. The CSF, which is under a positive pressure due to blood pressure, respiration, and positioning of the animal, begins to flow out of the needle entry site once the micro needle is removed. The micro needle then is pulled slowly backwards and the narrow bore pipette is used to collect the CSF as it exits the compartment. Once the needle is completely removed, the pipette is lowered into the puncture site and used to remove any remaining CSF. The primary collection usually takes less than 15 seconds for completion. The cistern will refill with several TL of CSF within two minutes. A second collection is performed to increase the net yield. At the end of the procedure, the emptied cistern is collapsed due to the removal of CSF. CSF is not collected past the first two minutes. The isolated CSF is transferred quickly into a pre-chilled polypropylene tube on ice. Less than 5% of samples contain visible blood contamination.

Example 26

Biochemical, Histochemical, Behavioral, and Toxicology Evaluations of Long-term NSAID Treatment When mice are sacrificed, one hemi-brain is processed for biochemical analyses and the other for immunohistochemical and histochemical analyses.

$A\beta_{40}$, $A\beta_{42}$, and total $A\beta$ levels in mice brains are determined. Both SDS-soluble and SDS-insoluble formic acid-soluble fractions are examined. ELISA, described in Kawarabayashi et al. (2001) *J Neur* 21:372–381, and the BAN50 system, described in Suzuki et al. (1994) *Sci* 264: 1336–1340, are used. Both $A\beta_{40}$ and $A\beta_{42}$ polyclonal capture antibodies and end-specific polyclonal antibodies are available. Changes in levels of different $A\beta$ species due to NSAID treatments are examined by imunoprecipitation-mass spectral analysis. $A\beta$ levels in plasma and CSF are determined at the time of sacrifice.

To examine total plaque burden, brain sections are stained with anti-$A\beta$ antibodies. Antibodies to all $A\beta$ species as well as end specific $A\beta_{40}$ and $A\beta_{42}$ antibodies are used. Cored plaques are detected by staining with thioflavin. Plaque number and amyloid burden are calculated as described in the Sigma ScanPro image analysis software (see Haugabook et al. (2000) *Faseb J*). Plaque types and extent of vascular and parenchymal amyloid depositions are examined.

Inflammation is examined by biochemical and histochemical techniques. Astrocytosis is examined using immunohistochemical staining and Western blotting of the SDS-extract for GFAP. Microglial activation is examined using staining techniques for anti-phophotyrosine as described in Lim et al. (2000) *J Neurosci* 20:5709–14. Alternatively, microglia are immunostained using a pan MHC antibody or using SMI-312 GS lectin as described in Frautschy et al. (1998) *Am J of Path* 152:307–17. Inflammatory markers such as α1ACT and APOE are examined using Western blot analysis of the SDS-extract, while IL-1 and IL-6 are examined using commercially available ELISA kits.

To examine neuronal loss and tau pathology, sections from brains are stained using haematoxylon and eosin. Sections are examined for overt pathological signs and neuronal loss. Marked neuronal loss is quantitated using stereological counting. Tau pathology is assessed using immunohistochemical staining by several anti-phosphorylated tau antibodies.

For behavioral studies, a modified version of the Morris watermaze is used to detect learning and memory impairments related to amyloidosis in mice over-expressing APP (see Chen et al. (2000) *Nature* 408:975–979). Testing is conducted in fully counterbalanced, age-matched squads of mice (five to seven per group); trial blocks are run at the same time each day, during the light cycle. Subjects run in a fixed order each day with an inter-trial interval of approximately fifteen minutes. Trial spacing minimizes effects of hypothermia and fatigue that often are seen in older animals (see Rick et al. (1996) *J Gerontol A Biol Sci Med Sci* 51 :B253–60). The first day of testing consists of swimming to a visible platform. This assesses motivation, and visual and swimming ability. One trial is performed from a fixed starting position to each of four separate cued platform locations. In subsequent days, up to ten trials per day are performed using a learning criterion of three consecutive trials with less than twenty escape latency (see Chen et al. (2000) *Nature* 408:975–979). No probe trial is necessary since the only dependent variable measured is trials to reach criterion (TTC). Once an animal reaches criterion on one platform location, it is immediately switched to a new location. Testing is continued until five platform locations have been learned. Deficits in TTC are apparent in this paradigm primarily on the last two platform locations. These data are used with neuropathological data to assess the mice (see Chen et al. (2000) *Nature* 40.8:975–979).

Evaluation of neurological and sensorimotor skills is performed on the first day of testing, before the cued platform trial. A standard test battery is administered. This consists of (a) ten minutes in an automated open field, (b) examination of righting and grasping reflexes, (c) latency to fall when suspended from a wire by the forepaws, and (d) rotorod performance. These tests screen basic functions such as strength, balance, and locomotor/exploratory behavior that can affect watermaze performance (Rick et al. (1996) *J Gerontol A Biol Sci Med Sci* 51: B253–60; Murphy et al. (1995) *Neur Learn Mem* 64:181–6; Bickford et al. (1997) *Neur Aging* 18, 309–18; Cammisuli et al. (1997) *Behav Brain Res* 89:179–90; and Lewis et al. (2000) *Nat Genet* 25:402–5). In this way, effects of strength, balance, and locomotor/exploratory behavior on watermaze performance are accounted for.

As in acute studies, appropriate plasma markers are tested intermittently on a few NSAID treated mice to monitor liver and renal functions in both preventative and therapeutic trails. Weights of the mice are monitored bi-weekly, and complete blood counts are performed every two to three months. At the time of sacrifice, the GI tract is examined for signs of ulceration using a dissecting microscope as described in Kalgutkar et al. (2000) *J of Med Chem* 43:2860–70.

Example 27

Determination of the Effects of NSAIDs on Aβ Deposition—Long-term Preventative Trial NSAIDs that selectively reduce $A\beta_{42}$ levels in acute studies are examined in a preventative trial to determine if they can prevent Aβ deposits. Six-month-old Tg2576 mice are used in preventative trials since Aβ deposit has not yet taken place. NSAID treatment of mice at this age corresponds to treating humans before signs of clinical disease occur.

Tg2576 mice are treated with experimentally optimized doses of NSAID for three, six, and twelve months. Each treatment group consists of a minimum of twenty animals, five of which are examined at each of the three time points. The remaining five mice are included in case of illness or death during long-term dosing. Three to four mice are placed into a treatment group each month until groups of twenty animals are established. At the time of sacrifice, tissues obtained for analysis are stored until all the mice within an experimental group have been sacrificed. Therefore, all samples from mice within one experimental group are examined simultaneously. For ibuprofen, naproxen, and control groups, twenty-seven mice are used per experimental group. The extra mice are treated for twelve months after which time behavioral patterns and additional pathologic parameters are examined.

The following NSAIDs are used in preventative trials: ibuprofen which reduces $A\beta_{42}$ levels, has anti-inflammatory activity, and has a short-half life; meclofenamic acid which is more potent at reducing $A\beta_{42}$ levels in vitro, and has anti-inflammatory activity; sulindac which reduces $A\beta_{42}$ levels, has anti-inflammatory activity, and has an extended-half-life; naproxen which has no effect on $A\beta_{42}$ levels, but has anti-inflammatory activity, and COX-1 and COX-2 inhibitory activities; and celecoxib which is an anti-inflammatory COX-2 selective agent. In addition, other NSAIDs that reduce $A\beta_{42}$ levels but show selectivity for this effect over inhibitory effects on COX-1, COX-2, or both are included in this study. At three, six, and twelve months of treatment with NSAIDs, mice are analyzed for behavioral alterations; then they are sacrificed and biochemical analyses are performed as described in Example 26.

Example 28

Alteration of Aβ Deposits by NSAIDs—Long Term Therapeutic Trial

To determine whether Aβ deposition, the effects of Aβ deposition, or both can be altered once Aβ has accumulated to a high level, NSAIDs that selectively reduce $A\beta_{42}$ levels in acute studies are examined in a therapeutic trial. Effects of treatment with NSAIDs that reduce $A\beta_{42}$ levels are compared to effects of treatment with NSAIDs that do not reduce $A\beta_{42}$ levels such as the non-selective COX inhibitor naproxen and the selective COX inhibitor celecoxib. Sixteen-month-old Tg2576 mice are treated with experimentally optimized doses of NSAIDs for three or six months. Sixteen-month-old mice have large amounts of Aβ in the brain and therefore, are representative of human patients with clinical signs of AD. Amyloid deposition, behavior, and AD-like pathology are examined as described in Example 26. Fourteen mice per treatment group are used; at least five treated and five control mice are compared.

Example 29

Statistical Analysis

Mann-Whitney and Dunnet's tests are used for comparisons between groups of treated and untreated mice. A number of correlative comparisons are made. Variables and outcomes used in statistical analysis for each study are the following. For in vitro screening experiments, variables include: Aβ levels in media, NSAID concentrations, toxicity, and COX inhibitory activity; while primary outcomes include reduction in Aβ$_{42}$ levels and COX inhibitory activity. In acute single-dose studies, variables include: Aβ levels in brain, plasma, and CSF; NSAID concentrations in plasma and brain; and dose of NSAID. Primary outcomes of acute single-dose studies include reduction in brain Aβ$_{42}$ levels and plasma levels of NSAID, while secondary outcomes includes correlation of brain, CSF, and plasma Aβ levels. In long-term studies, variables include: Aβ levels in brain, plasma, and CSF; NSAID concentrations in plasma (and brain, if possible); dose of NSAID; amyloid burden; extent of inflammatory response; behavioral performance; and toxicity. Primary outcomes of long-term studies include effects on Aβ levels in the brain, while secondary outcomes include evaluation of inflammatory response, behavior, toxicity, and correlative analyses.

Example 30

Clinical Investigations in Amyloid-reducing Actions of NSAIDs

The most promising FDA-approved NSAIDs, determined by preclinical studies, are examined for amyloid reducing actions in healthy subjects as well as subjects with mild to moderate Alzheimer's disease (AD). These studies are performed in three-group parallel design; each group consists of twelve subjects. Subjects are treated with an NSAID or a matching placebo several times a day, depending on the NSIAD, for fourteen days. Study NSAIDs are purchased and over-encapsulated by the San Diego VAMC Pharmacy service or by another compounding pharmacy. Placeboes are similarly encapsulated.

AD subjects are selected based on the following criteria. Subjects consist of men and women, ages 60–85, who are diagnosed with probable AD using the National Institute of Neurologic Communicative Disorders and Stroke-Alzheimer's Disease and Related Disorders Association (NINCDS-ADRDA) test (McKhann et al. (1984) *Neurology* 34:939–944) or have mild to moderate dementia as determined by the Mini-Mental State Examination (MMSE, Mohs et al. (1996) *Int Psychogeriatr* 8:195–203). MMSE scores in the range of 15–25 indicate mild to moderate dementia. AD subjects have caregivers that can ensure compliance with medication regimens and with study visits and procedures.

Non-demented control subjects consist of men and women ages 60–80. Control subjects lack significant cognitive or functional complaints, or depression as determined by the Geriatric Depression Scale (GDS), and have MMSE scores in the range of 27–30. Control subjects have the same general requirements as AD subjects with the exception that caregivers are not required. Both AD subjects and control subjects have good general health, i.e., subjects do not have serious or life-threatening comorbid conditions.

Subjects who have medically active major inflammatory comorbid condition(s) such as rheumatoid arthritis, or those who have peptic ulcer, gastro-intestinal bleeding, or intolerance of NSAIDs in the past are excluded from the study. Those who have contra-indications to lumbar puncture, such as severe lumbar spine degeneration, sepsis in the region of the lumbar spine, or a bleeding disorder are excluded from participation in the study. In addition, subjects who currently or recently use medications such as NSAIDs, prednisone, or immunosuppressive medications such as cyclophosphamide that could interfere with the study are excluded. Recently is defined as within one month before undergoing the baseline visit (see next paragraph). Subjects undergoing acetylcholinsterase inhibitor (AChE-I) treatments for AD are not excluded if these subjects have been on stable doses for at least four weeks. Similarly, AD subjects taking antioxidants such as vitamin E, vitamin C, or Gingko biloba are not excluded if they have been on stable doses for at least four weeks. Subjects who use NSAIDs or aspirin on a regular basis are excluded. If needed, analgesics such as paracetamol (Tylenol) are provided during the fourteen-day study.

The study procedure consists of three in-clinic visits: an initial screening visit, a baseline visit, and a follow-up visit at fourteen days. During the screening visit, information needed to assess eligibility is obtained and MMSE is administered.

During the baseline visit, which takes place within two weeks of the screening visit, physical examinations and lumbar punctures are performed. Blood samples are drawn for laboratory tests such as APO-E genotyping and for plasma preparation (see Example 31). At this time, subjects or caregivers, in the case of AD subjects, are given a fourteen-day supply of study NSAID along with instructions about timing of doses and potential adverse effects. (For AD subjects, caregivers are required to accompany subjects to each visit, and are responsible for monitoring and supervising administration of study NSAIDs.) A calendar is provided on which times of medications and potential adverse symptoms are recorded.

The NSAID treatment regimen consists of a fourteen-day treatment with NSAIDs in the form of capsules taken two or three times a day with meals. A high and a low study dose of NSAID are used. For ibuprofen, study doses of 800 mg and 400 mg are used. A study dose of 800 mg consists of two 400 mg ibuprofen tablets, while a study dose of 400 mg consists of one 400 mg ibuprofen capsule and one placebo capsule. For sulindac, a study dose of 200 mg twice a day for a total of 400 mg per day is used. For meclofenamic acid, study doses of 100 mg and 400 mg per day are tested. NSAIDs are pre-packed into a day-by-day plastic medication dispenser.

During the follow-up visit, twelve or fourteen days after beginning treatment, vital signs and adverse side effects of study NSAIDs are assessed. Surplus NSAIDs are returned and counted. In addition, lumbar punctures are performed and blood samples are drawn for laboratory tests and for plasma preparations.

Visits during which lumbar punctures are performed and blood samples are drawn are scheduled for mornings with overnight fasting to avoid obtaining post-prandial or hyperlipemic plasma samples, which can influence levels of Aβ$_{40}$ and Aβ$_{42}$. Table 4 summarizes biological markers that are analyzed from plasma and CSF samples.

TABLE 4

Plasma and CSF biological markers

| Assay | Method | Volume of CSF | Volume of Plasma |
|---|---|---|---|
| Protein, glucose, cells | | 1 mL | |
| Aβ$_{40}$ | ELISA | 100 TL × 2 (in duplicate) | 100 TL × 2 |

TABLE 4-continued

Plasma and CSF biological markers

| Assay | Method | Volume of CSF | Volume of Plasma |
|---|---|---|---|
| Aβ$_{42}$ | ELISA | 100 TL × 2 (in duplicate) | 100 TL × 2 |
| Aβ$_{38}$ | Mass Spectrometry | 1 mL | |
| Isoprostanes | Gas Chromatography/ Mass Spectrometry | 2 mL | |
| M-CSF | ELISA | 50 TL × 2 (in duplicate) | |
| MCP-1 | ELISA | 50 TL × 2 (in duplicate) | |
| Tau, | ELISA | 50 TL × 2 (in duplicate) | |
| P-tau181 | | 50 TL × 2 (in duplicate) | |
| Plasma levels of NSAIDs | HPLC | | 1 mL |

Example 31

Collection of Plasma and CSF

Plasma samples are prepared within 15–30 minutes after blood samples are drawn. Plasma samples are frozen at −70° C. until used. At least 6 mL of CSF and, whenever possible, 10–15 mL are drawn from each subject. Total cell, protein, and glucose estimations are performed. Samples are identified by a study ID number, and technicians who run ELISAs or other assays are blinded to the identity of the subjects or the treatment conditions.

Example 32

Specific Assays

ELISA is used to determine Aβ$_{40}$ and Aβ$_{42}$ levels in CSF. Batches of samples are assayed simultaneously in duplicate on microplates according to established procedures (3). In Aβ$_{42}$ detection, two antibodies are used: (1) a monoclonal antibody that recognizes an epitope within the first five amino acids of Aβ is used for capture and (2) an end-specific monoclonal antibody that recognizes Aβ ending at amino acid 42 and conjugated to horse radish peroxidase is used for detection. CSF levels of Aβ$_{38}$ are measured by mass spectroscopy as described in Example 6. CSF isoprostanes are measured by gas-chromatography/negative chemical ionization mass spectroscopy using internal standards for calibration Montine et al. (1999) *Neurology* 52:562–565). CSF levels of MCSF, MCP-1, tau, and P-tau 181 are determined. Commercially available ELISA kits are used for M-CSF (R&D Diagnostics) and MCP-1 (Pharmingen, San Diego) determinations. CSF tau and P-tau181 are determined using ELISA kits from Innogenetics, Inc., Plasma levels of specific NSAIDs are determined by HPLC methods described in published procedures (Canaparo et al. (2000) *Biomed Chromatogr* 14:219–26).

Example 33

Analysis of Clinical Data

Reduction in Aβ$_{42}$ levels due to NSAIDs treatment is detected as decreases in Aβ$_{42}$ levels in CSF and/or plasma. Therefore, subjects with AD or elderly control subjects who receive NSAID treatments show serial decreases in CSF and/or plasma Aβ$_{42}$ levels, while those who take a placebo will not show serial changes in CSF and/or plasma Aβ$_{42}$ levels.

To assess comparability between groups of subjects at baseline, demographic data (e.g. age and gender), dementia severity (MMSE score), and APO-E e4 allele frequency are compared between placebo groups, and groups of subjects with AD or elderly controls that are treated with NSAIDs. Continuous variables are compared by ANOVA and frequencies of categorical variables such as gender and APO-E genotype are compared using Chi-squared or Fisher's exact test.

Changes in levels of biomarkers of interest between baseline samples to follow-up samples are calculated for each subject. Descriptive statistics are used to determine whether levels of biomarkers at baseline are normally distributed. If they are, then mean changes in each treatment group are compared with each placebo group using ANOVA. If they are not normal, then data transformation is applied or non-parametric statistics are used to compare changes in biomarker levels between different groups of subjects.

To determine whether changes in Aβ$_{42}$ levels are accompanied by changes in Aβ$_{40}$ and Aβ$_{38}$ levels, CSF Aβ levels in placebo groups are compared to that in treatment groups using ANOVA. Levels of biomarkers related to microglial function (e.g. M-CSF and MCP-1), oxidative damage in the brain (e.g. F-2 isoprostanes), and neuronal degeneration (e.g. tau and P-tau181) are compared before and after treatment as well as between groups treated with placebo or with NSAID. If levels of biological markers change after treatment with NSAID, the change is examined in relation to variables such as age, gender, APO-E genotype, and plasma NSAID levels. Scatter-plots and appropriate statistical comparisons are used.

Example 34

Statistical Power Calculations

Published data indicate that CSF Aβ$_{42}$ levels remain stable on repeated lumbar punctures. The power to detect differences between subjects treated with NSAIDs and subjects treated with placeboes depends on magnitudes of changes in biomarker levels after treatment relative to baseline.

In published longitudinal data for CSF Aβ$_{42}$ levels in an AD patient group of 53 (see Andreasen et al. (1999) *Arch Neurol* 56:673–80), baseline CSF Aβ$_{42}$ level (mean±SD) was 709±304 pg/mi and follow-up (10 months later) CSF Aβ$_{42}$ level was 701±309 pg/mL. The correlation between the first and second CSF Aβ$_{42}$ level was R=0.90. No published longitudinal CSF Aβ$_{42}$ data are available in healthy subjects. In two studies that included healthy subjects, the values for CSF Aβ$_{42}$ levels were 1485±473 pg/mL (see Galasko et al. (1998) *Arch Neurol* 55:937–45) and 1678±436 pg/mL (see Andreasen et al. (1999) *Arch Neurol* 56:673–80).

The power calculation uses the following assumptions: (1) levels are stable over time as described in Andreasen et al. (1999) *Arch Neurol* 56:673–80 and (2) variance of change is similar. The standard deviation is calculated as square root of ((1-correlation)*2*SD^2). A pre-post correlation of 0.8 for CSF Aβ$_{42}$ level is assumed.

If the change in pre-post mean CSF Aβ levels is assumed to be approximately zero in the placebo group, then effect size depends on the mean level of $A\beta_{42}$ at baseline. For example, for elderly controls, if the mean CSF $A\beta_{42}$ level is 1485 pg/mL (see Galasko et al. (1998) *Arch Neurol* 55:937–45), then a 0.25 effect size represents an increase or decrease of the mean by 371 pg/mL due to treatment.

For power calculations, the following are assumed: (1) alpha=0.05, (2) power=0.80, and (3) two-group studies in which equal numbers of subjects exposed to placebo and treatment are used. For power calculations with an effect size of 0.25, a sample size (N) of 11 in each of the two groups is required. With effect size of 0.2, an N of 16 is required in each group.

Twelve subjects per group are used for each study allowing for detection of an effect size of 0.25 or higher. In pre-clinical studies, several NSAIDs (including ibuprofen and meclofenamic acid) reduced $A\beta_{42}$ levels in supernatants from cultured cells and in brain tissues of transgenic mice by over 25%. In long-term transgenic mouse studies using ibuprofen, reported in (Lim et al. (2000) *J Neurosci* 20:5709–14), $A\beta$ levels in the brain were about 38% lower when treated than untreated.

If the variance in CSF $A\beta_{42}$ levels between subjects or on repeated lumbar puncture is greater than in these projections, then sample size is re-assessed and group size is modified as needed. A similar set of calculations using published data on CSF $A\beta_{42}$ levels in AD patients shows that groups of twelve patients are sufficient to detect a 25% effect size.

Published longitudinal CSF data are available for CSF tau in AD. Sunderland et al. (1999) *Biol Psychiatry* 46:750–755 studied twenty-nine patients with AD having baseline CSF tau (mean±SD) of 548±355 pg/mL, follow-up CSF tau at twelve months of 557±275 pg/mL, and an R-value of 0.85.

The decision to use twelve subjects per group is derived from $A\beta$ data. Again, assuming CSF tau remains stable and unchanged on average in the absence of treatment, an effect size for a decrease in CSF tau by at least 33% relative to baseline is 183 pg/mL of tau.

In a two-group study design with (1) equal subject numbers receiving placebo and treatment, (2) N=12 per group, and (3) assuming $\alpha=0.05$, then power is 73% for detecting an effect size of 33% or greater for tau.

With the exception of plasma AD levels that remained stable as indicated by preliminary ibuprofen studies, the degree of variation of longitudinal measurements of other biomarkers is not known. Ibuprofen studies in healthy elderly and subjects with mild AD are performed first, then sample sizes are reassessed for all biomarkers measured and necessary changes are incorporated in to other NSAID studies.

Example 35

Placebo-controlled Study of NSAIDs with $A\beta$-lowering Actions

A double-blind randomized placebo-controlled study is performed using sixty AD subjects treated with a placebo, ibuprofen, or another FDA-approved NSAID with $A\beta$-reducing action at a well-tolerated dose for 48 weeks. Specific NSAIDs and doses are selected based on results obtained in Example 30.

Subjects are 50–90 years of age and have diagnoses of probable AD as indicated by the NINCDS-ADRDA test. Subjects have an MMSE range of 15–25, good general health, i.e., no life threatening or major medical illnesses; and caregivers who can supervise medication regimens and provide collateral information. Additional screening criteria are as described in Example 30.

Initially, subjects are assessed for eligibility in a screening visit. MMSEs and physical examinations are performed. Blood samples are obtained for routine laboratory tests. Block randomization is used to assign patients to placebo or active treatment groups. Assignment is determined according to baseline MMSE scores so that dementia severity is similar in the placebo and active treatment groups.

During the baseline visit, scheduled within two weeks of the screening visit, vital signs are assessed, lumbar punctures are performed, and blood samples are drawn for APO-E genotyping and for plasma preparation (see Example 31). CSF levels of $A\beta_{40}$, $A\beta_{42}$, isoprostanes, tau, and P-tau as well as plasma levels of $A\beta_{40}$ and $A\beta_{42}$ are determined. In addition, cognition is assessed using the Alzheimer's Disease Assessment Scale—cognitive component (ADAS-cog, see Galasko et al. (1997) *Alzheimer Dis Assoc Disord* 11; Suppl 2:S33–9) and MMSE, while functional ability is assessed using the Alzheimer's Disease Cooperative Study Activities of Daily Living Scale (ADCS-ADL) (see McKhann et al. (1984) *Neurology* 34:939–944). At this time, caregivers of subjects are given a twelve-week supply of study NSAID along with instructions on timing of doses and potential adverse effects.

At the 12-week visit, vital signs, stool guaiac, and adverse side effects are assessed. Unused NSAID is counted. At the 24-week visit, assessment procedures identical to those of the baseline visit are performed. A count of unused NSAIDs and an inquiry about adverse events are made. At the 36-week visit, assessment procedures identical to the 12-week visit are performed, while at the 48-week visit, assessment procedures identical to those of the baseline visit are performed. A count of unused NSAIDs and inquiry about adverse events are made. Table 5 summarizes the examinations performed at each visit in the study.

TABLE 5

Schedule of events

| | Screen | Baseline | 12 week | 24 week | 36 week | 48 week |
|---|---|---|---|---|---|---|
| Check entry criteria, obtain consent | X | | | | | |
| Screening blood tests | X | | | | | |
| Demographics, medical history | X | | | | | |
| Vital signs | X | X | X | X | X | X |
| Rectal examination, stool guaic | X | | X | X | X | X |
| MMSE | X | X | | X | | X |
| ADAS-cog, ADCS ADL | | X | | X | | X |
| Dispense medications | | X | X | | X | |
| Adverse events, pill count | | | X | X | X | X |
| Lumbar puncture, plasma for $A\beta$ | | X | | X | | |
| Blood drawn for safety laboratory tests | | X | | X | | X |

In addition, each subject/caregiver is interviewed by telephone at 4, 8, 16, and 20 weeks to inquire about continuation in the study, medication usage, and adverse events.

Example 36

Statistical Analyses of Placebo-controlled Studies

Statistical analyses involve the comparison of cognitive (ADAS-cog, MMSE), functional (ADCS-ADL), and biomarker data of subjects before and after treatment. Subjects treated with NSAID for 48 weeks are expected to exhibit less cognitive and functional decline relative to subjects who are treated with placebo. NSAID treatments are expected to associate with improved biomarker indices in CSF and possibly in plasma.

Differences ($\Delta$s) between final and initial ADAS-cog and ADCS-ADL scores are referred to as primary outcome measures. Mean $\Delta$s for placebo and treatment groups are compared by ANOVA. To control for subjects who fail to complete the study, a Last Observation Carried Forward (LOCF) analysis is performed.

Changes in CSF levels of $A\beta_{42}$, tau, P-tau181, F-2-isoprostanes, and plasma $A\beta_{42}$ and $A\beta_{40}$ are similarly analyzed as outcome measures using ANOVA, or a non-parametric test (e.g. Kruskal-Wallis) if the data are not normal. Correlations between changes in biomarker measures and in clinical measures at 24 weeks are examined by scatter-plots and correlational analyses.

Example 37

Cell Culture Studies of Flurbiprofen

Figure 14:
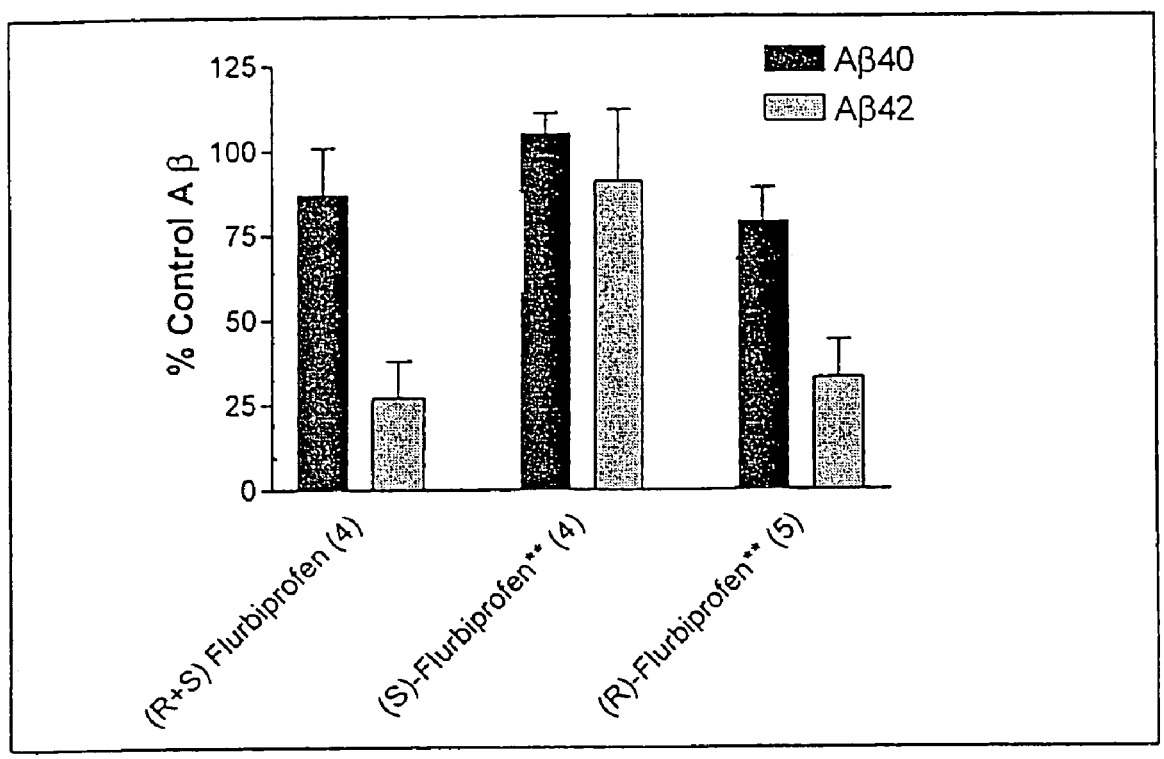
FIG. 14 is a bar graph illustrating the effect of NSAIDs on $A\beta_{42}$ production in H4 APP 695 wild type cells. Cells treated with the vehicle (DMSO) alone were used as controls.

APP695-transfected H4 cells were treated with either the R or S enantiomers of flurbiprofen or with racemic mixtures (R+S) of flurbiprofen. Similar effects on $A\beta_{42}$ production were observed in APP695-transfected H4 cells as shown in FIG. 14. $A\beta_{42}$ levels were lowered by 50% in the presence of 100 TM of the racemic mixture. Similarly, $A\beta_{42}$ levels were lowered by 20% in the presence of 10 TM of R-flurbiprofen, 49% in the presence of 100 TM R-flurbiprofen, and $A\beta_{42}$ levels were lowered by 58% in the presence of 100 TM S-flurbiprofen. In contrast, levels of $A\beta_{40}$ production by these cells were not altered when the cells were exposed to the R, S, or racemic mixture of flurbiprofen.

Example 38

Acute Dosing in T2576 Mice

Figure 15:
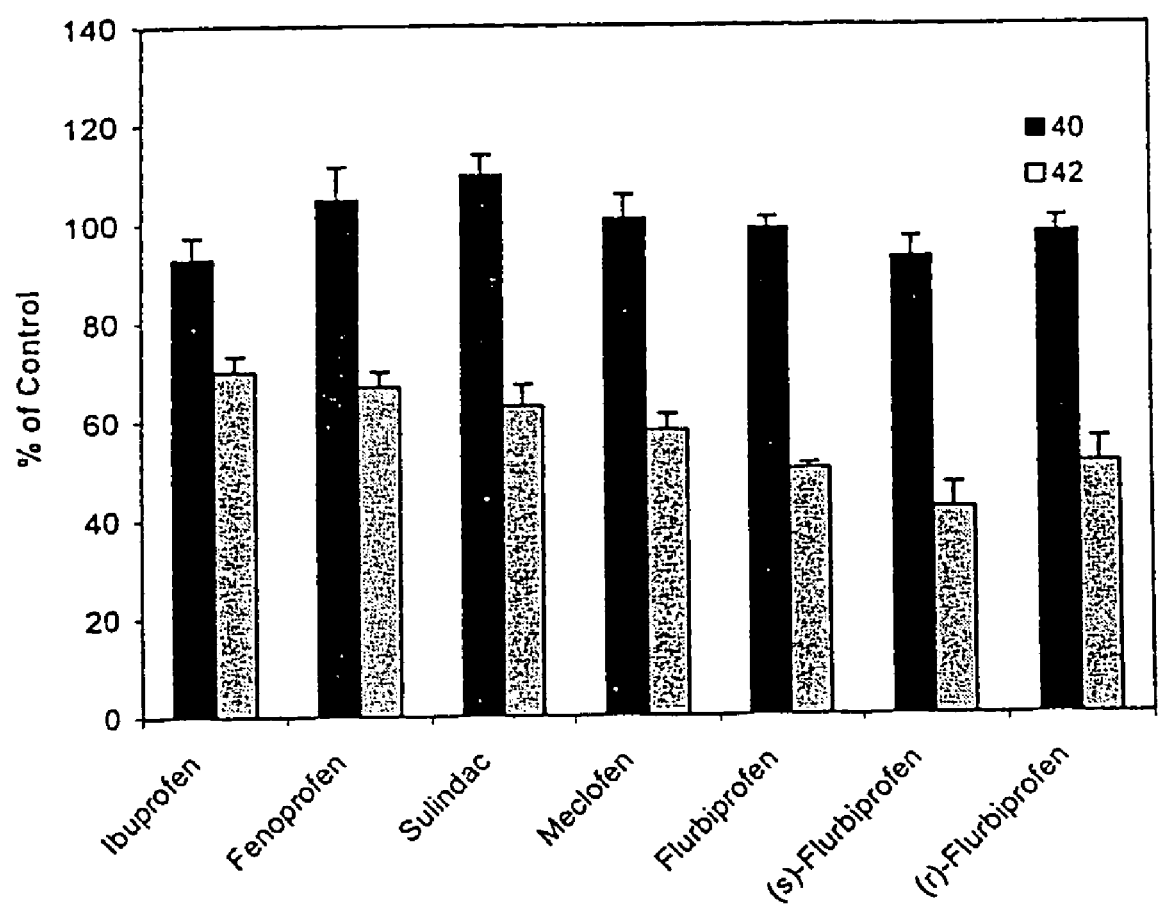
FIG. 15 is a bar graph comparing the effect of the S and R enantiomers of flurbiprofen and the effect of a mixture of R+S enantiomers on brain $A\beta_{42}$ levels in Tg2576 mice. Data are expressed as a % of the control. Both the mixture of R+S enantiomers and R-flurbiprofen alone lower $A\beta_{42}$ levels in 3-month old Tg2576 mouse brains (p<0.01).

Three-month old Tg2576 mice were treated for three days with 100 mg/kg/day of R-flurbiprofen, S-flurbiprofen, or the racemic mixture (R+S) flurbiprofen. Compounds were administered orally. Levels of $A\beta_{42}$ in brains of animals treated with flurbiprofen were compared with those treated with vehicle alone. As shown in FIG. 15, R-flurbiprofen was more effective at lowering brain $A\beta_{42}$ in this acute dosing paradigm than S-flurbiprofen. In contrast, R-flurbiprofen and the racemic mixture had a similar effect on $A\beta_{42}$ levels in mice brains.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of identifying an $A\beta_{42}$ lowering agent that reduces the ratio of $A\beta_{42}$ to $A\beta_{40}$ comprising the steps of:
   (a) identifying a candidate $A\beta_{42}$ lowering agent which is a non-steroidal anti-inflammatory drug (NSAID), NSAID derivative, or NSAID analogue;
   (b) contacting said candidate $A\beta_{42}$ lowering agent with a biological composition that produces $A\beta_{42}$ and $A\beta_{40}$;
   (c) comparing the ratio of $A\beta_{42}$ to $A\beta_{40}$ in said biological composition contacted with said candidate $A\beta_{42}$ lowering agent to the ratio of $A\beta_{42}$ to $A\beta_{40}$ in a biological composition not contacted with said candidate $A\beta_{42}$ lowering agent; and
   (d) identifying said candidate A$\beta$42 lowering agent as a selective $A\beta_{42}$ lowering agent if a reduction in the ratio of $A\beta_{42}$ to $A\beta_{40}$ in said biological composition contacted with said candidate $A\beta_{42}$ lowering agent is observed when compared with the ratio of $A\beta_{42}$ to $A\beta_{40}$ in said biological composition not contacted with said candidate $A\beta_{42}$ lowering agent.

2. The method of claim 1, wherein said biological composition that produces $A\beta_{42}$ and $A\beta_{40}$ comprises a cell-free composition, an in vitro cell-based composition, or an in vivo animal-based composition.

3. The method of claim 2, wherein said biological composition is an in vitro cell-based composition.

4. The method of claim 3, wherein said in vitro cell-based biological composition is a cell culture, and said ratio is the ratio of secreted $A\beta_{42}$ to $A\beta_{40}$ ratio.

5. The method of claim 3, wherein said in vitro cell-based biological composition comprises cells that express one or more familial Alzheimer's disease genes selected from the group consisting of a mutant amyloid precursor protein (APP) gene, a mutant presenilin-1 gene, and a mutant presenilin-2 gene.

6. The method of claim 3, wherein said in vitro cell-based biological composition comprises cells that express a mutant amyloid precursor protein (APP) having the Swedish mutation (APP695NL).

7. The method of claim 4, wherein the cells of said cell culture secrete one or more A$\beta$ peptides selected from the group consisting of $A\beta_{34}$, $A\beta_{36}$, $A\beta_{37}$, $A\beta_{38}$, $A\beta_{39}$, $A\beta_{40}$ and $A\beta_{42}$.

8. The method of claim 4, wherein the cells of said cell culture secrete $A\beta_{42}$.

9. The method of claim 1, wherein the step of comparing the ratio of $A\beta_{42}$ to $A\beta_{40}$ produced by said biological composition comprises determining the level of $A\beta_{42}$ and $A\beta_{40}$ with one or more techniques selected from the group consisting of an immunoprecipitation, western hybridization, sandwich enzyme-linked immunosorbent assays (ELISA), and mass-spectrometry.

10. The method of claim 1, wherein said $A\beta_{42}$ to $A\beta_{40}$ ratio is determined by measuring $A\beta_{42}$ and $A\beta_{40}$ levels with an antibody based assay.

11. The method of claim 1, wherein said biological composition comprising mammalian cells expressing APP are cultured under conditions that allow for APP expression, APP processing, and $A\beta_{42}$ secretion from said mammalian cells.

12. The method of claim 1, wherein said biological composition comprises a cell line that expresses an APP selected from the group consisting of APP695 and APP751.

13. The method of claim 8, wherein said cells are selected from the group consisting of CHO cells, human neuroglioma cells, fibroblast cells, HEK293 cells, and HS683 cells.

14. The method of claim 1, wherein said $A\beta_{42}$ lowering agent does not substantially change the level of $A\beta_{40}$.

15. The method of claim 1, wherein said NSAID is selected from the group consisting of amino aryl carboxylic acid, aryl acetic acid, and aryl propionic acid.

16. The method of claim 1, wherein said NSAID derivative is selected from the group consisting of a derivative of an amino aryl carboxylic acid, a derivative of an aryl acetic acid, and a derivative of an aryl propionic acid.

17. The method of claim 1, wherein said NSAID analogue is selected from the group consisting of an analogue of an amino aryl carboxylic acid, an analogue of an aryl acetic acid, and an analogue of an aryl propionic acid.

18. The method of claim 1, wherein said NSAID, NSAID derivative, or NSAID analogue is selected from the group consisting of 5-nitro-2-(3-phenylpropylamino) benzoic acid (NPPB), mefenamic acid, o-(acetoxyphenyl) hept-2-ynyl sulphide (APHS), reservatrol, SC560, NS398, guaiazulene, ketorolac, benzylamine, ketoprofen, fenbufen, isoixicam, tenoxicam, tolfenamic acid, acemetacin, niflumic acid, dapsone, sulindac sulfone, nimesulide, suxibuzone, acetylsalicyclic acid, salicylic acid, carprofen, celecoxib, rofecoxib, fenoprofen, flurbiprofen, ibuprofen, naproxen, sulindac, sulindac sulfide, diclofenac, piroxicam, ketoprofen, diflunisal, nabumetone, etodolac, oxaprozin, meloxicam, flufenamic acid, meclofenamic acid, and indomethacin.

19. The method of claim 1, wherein said candidate $A\beta_{42}$ lowering agent is a derivative or analogue of a NSAID selected from meclofenamic acid and flufenamic acid, wherein said NSAID derivative or analogue is modified from said NSAID by altering the position of the carboxylic acid group on the phenyl ring of said NSAID, altering the position or type of substituents on the phenyl ring opposite the carboxylic acid group of said NSAID, altering the bond connecting the two phenyl rings of said NSAID, altering the carboxylic acid group of said NSAID to propionic acid or another substituent, or performing any combination of these alterations, to generate a candidate $A\beta_{42}$ lowering agent.

20. The method of claim 1, wherein said candidate $A\beta_{42}$ lowering agent is a derivative or analogue of a NSAID selected from fenoprofen, flurbiprofen, and carprofen, wherein said NSAID derivative or analogue is modified from said NSAID by altering the position of the propionic acid group on the phenyl ring of said NSAID, altering the position or type of substituents on the phenyl ring opposite the propionic acid group or said NSAID, altering the bond connecting the two phenyl rings of said NSAID, altering the acetic acid group of said NSAID to carboxylic acid or another substituent, or performing any combination of these alterations, to generate a candidate $A\beta_{42}$ lowering agent.

21. The method of claim 1, wherein said candidate $A\beta_{42}$ lowering agent is a derivative or analogue of indomethacin, wherein said indomethacin derivative or analogue is modified from said indomethacin by altering the carboxylic acid group of indomethacin to another substituent, altering the indole nitrogen to another substituent, or performing any combination of these alterations to generate a candidate $A\beta_{42}$ lowering agent.

22. The method of claim 1, wherein said candidate $A\beta_{42}$ lowering agent is a derivative or analogue of sulindac sulfide, wherein said sulindac sulfide derivative or analogue is modified from said sulindac sulfide by altering the methylthiol group of sulindac sulfide to another substituent, altering the propionic acid group of sulindac sulfide to another substituent, altering the fluoride moiety of sulindac sulfide to another substituent, or performing any combination of these alterations, to generate a candidate $A\beta_{42}$ lowering agent.

* * * * *